(12) United States Patent
Matsuo et al.

(10) Patent No.: US 8,277,729 B2
(45) Date of Patent: Oct. 2, 2012

(54) SAMPLE ANALYZER, REAGENT ASPIRATING METHOD, AND COMPUTER PROGRAM PRODUCT

(75) Inventors: Naohiko Matsuo, Kobe (JP); Hiroyuki Fujino, Kakogawa (JP); Takamichi Naito, Kobe (JP); Nobuhiro Kitagawa, Akashi (JP)

(73) Assignee: Sysmex Corporation, Kobe (JP)

( * ) Notice: Subject to any disclaimer, the term of this patent is extended or adjusted under 35 U.S.C. 154(b) by 772 days.

(21) Appl. No.: 12/079,789

(22) Filed: Mar. 27, 2008

(65) Prior Publication Data

US 2008/0241939 A1 Oct. 2, 2008

(30) Foreign Application Priority Data

Mar. 29, 2007 (JP) .................. 2007-089300

(51) Int. Cl.
*G01N 15/06* (2006.01)
*G01N 33/00* (2006.01)
*G01N 33/48* (2006.01)

(52) U.S. Cl. ............... 422/64; 422/50; 422/63; 422/65; 422/66; 422/67; 422/82; 422/82.01; 422/82.05; 422/68.1; 436/43; 436/47; 436/54; 436/63; 436/66; 436/67; 436/68; 436/69; 436/70; 436/71; 436/174; 436/180

(58) Field of Classification Search ............... 422/50, 422/63, 64, 65, 66, 67, 81, 82, 82.01, 82.05, 422/68.1; 436/43, 47, 54, 63, 66, 67, 68, 436/69, 70, 71, 174, 180

See application file for complete search history.

(56) References Cited

U.S. PATENT DOCUMENTS

| | | | |
|---|---|---|---|
| 2004/0101440 A1* | 5/2004 | Ishizawa et al. | 422/64 |
| 2005/0047964 A1 | 3/2005 | Nishida et al. | |
| 2005/0053521 A1* | 3/2005 | Hirayama | 422/67 |
| 2005/0084426 A1 | 4/2005 | Mimura et al. | |
| 2005/0196821 A1* | 9/2005 | Monfre et al. | 435/14 |
| 2006/0029520 A1* | 2/2006 | Tanoshima et al. | 422/63 |
| 2006/0210438 A1* | 9/2006 | Nagai et al. | 422/73 |
| 2007/0078631 A1* | 4/2007 | Ariyoshi et al. | 702/189 |
| 2007/0110617 A1* | 5/2007 | Nagai et al. | 422/65 |
| 2008/0056944 A1* | 3/2008 | Nakamura et al. | 422/67 |
| 2008/0187951 A1* | 8/2008 | Nagai et al. | 435/29 |
| 2008/0206098 A1* | 8/2008 | Tsutsumida et al. | 422/67 |
| 2009/0035873 A1* | 2/2009 | Shibata | 436/179 |

\* cited by examiner

*Primary Examiner* — Brian J Sines
(74) *Attorney, Agent, or Firm* — Brinks Hofer Gilson & Lione

(57) ABSTRACT

The present invention is to present a sample analyzer which is capable of respond immediately when a need to perform analysis of multiple items arises. The sample analyzer 1 includes a table 12 capable of holding a first rack 320 and a second rack 330; a reagent dispensing arm 120 which comprises a pipette part 121; a reagent dispensing driving section 120a for moving the reagent dispensing arm 120; a reagent barcode reader 350; and a control section 501 for controlling the reagent dispensing driving section 120a so as to move the pipette part 121 to a predetermined reagent aspirating position according to the identification information obtained by the reagent barcode reader 350.

18 Claims, 20 Drawing Sheets

Second reagent container rack 320 (rack type 1)

Third reagent container rack 330 (rack type 2)

Rack type 3

SAMPLE ANALYZER, REAGENT ASPIRATING METHOD, AND COMPUTER PROGRAM PRODUCT

RELATED APPLICATIONS

This application claims priority under 35 U.S.C. §119 to Japanese Patent Application No. 2007-089300 filed Mar. 29, 2007, the entire contents of which are hereby incorporated by reference.

FIELD OF THE INVENTION

The present invention relates to a sample analyzer for analyzing samples such as blood and blood plasma using a reagent according to predetermined analysis items, a reagent aspirating method for aspirating the reagent, and a computer program product.

BACKGROUND

A sample analyzer for analyzing samples such as blood and blood plasma using a plurality of reagents is conventionally known.

In recent years, the number and types of reagent containers to be arranged in the reagent arranging section of the sample analyzer are increasing to increase the number of measurement items and to improve the processing speed. There are also the needs of the user to use reagent containers of various sizes according to the usage state of the reagent.

However, if the number of reagent containers that can be arranged in the reagent arranging section is simply increased, the mechanism of the reagent arranging section enlarges, whereby the necessity to enlarge the device arises.

U.S. Patent Publication No. 2005-084426 discloses a sample analyzer using a reagent cassette in which two reagent containers for one measurement item are fixed with a connecting tool, and in which a barcode label recorded with information of the reagent contained in the two reagent containers and information of the respective aspirating position of the two reagent containers is provided, as described in FIG. 2 and paragraph.

However, in an automatic analyzer described in U.S. Patent Publication No. 2005-084426, in order to respond analysis of multiple items, a reagent cassette in which plurality of reagent containers is fixed with the connecting tool must be prepared in great numbers in advance, and the barcode label recorded with information of the type of the cassetted reagent and the aspirating position of the reagent container must be prepared. Thus, when a need to perform analysis of multiple items arises, it becomes difficult to respond immediately.

BRIEF SUMMARY

A first aspect of the present invention is a sample analyzer for analyzing a sample using a reagent corresponding to a predetermined analysis item, comprising: a table capable of holding a first rack which comprises a rack identifier and is capable of holding a reagent container, and a second rack which comprises a rack identifier and is capable of holding a reagent container, a shape of the second rack being different from that of the first rack; an aspirator which comprises an aspirating pipette in which a reagent from a reagent container on the table is aspirated and a driver for moving the aspirating pipette; an identification information obtainer for obtaining identification information of a rack holding a target reagent container which contains a target reagent used for analysis, from a rack identifier of the rack; and a controller for controlling the driver so as to move the aspirating pipette to a predetermined reagent aspirating position according to the identification information obtained by the identification information obtainer.

A second aspect of the present invention is a reagent aspirating method, comprising steps of: (a) obtaining identification information specifying a reagent container rack from rack identifiers of first and second reagent container racks held by a circular rotating table, and obtaining identification information specifying a reagent from a reagent identifier of each reagent container held in a plurality of reagent container holders of the first and second reagent container racks; (b) obtaining position information of reagent containers on the rotating table based on the identification information obtained in step (a); (c) moving an aspirating pipette to a first reagent aspirating position and rotating the rotating table so as to move a target reagent container containing a target reagent used for analysis to the first reagent aspirating position, when a reagent container rack holding the target reagent container is a first reagent container rack, based on position information of the target reagent container obtained in step (b), and moving the aspirating pipette to a second reagent aspirating position and rotating the rotating table so as to move the target reagent container to the second reagent aspirating position, when the reagent container rack holding the target reagent container is the second reagent container rack, based on the position information of the target reagent container obtained in step (b).

A third aspect of the present invention is a computer program product for enabling a computer to execute a reagent aspirating method, comprising: a computer readable medium; and software instructions, on the computer readable medium, for enabling the computer to perform predetermined operations comprising: (a) obtaining identification information specifying a reagent container rack from rack identifiers of first and second reagent container racks held by a circular rotating table, and obtaining identification information specifying a reagent from a reagent identifier of each reagent container held in a plurality of reagent container holders of the first and second reagent container racks; (b) obtaining position information of reagent containers on the rotating table based on the identification information obtained in step (a); (c) moving an aspirating pipette to a first reagent aspirating position and rotating the rotating table so as to move a target reagent container containing a target reagent used for analysis to the first reagent aspirating position, when a reagent container rack holding the target reagent container is a first reagent container rack, based on position information of the target reagent container obtained in step (b), and moving the aspirating pipette to a second reagent aspirating position and rotating the rotating table so as to move the target reagent container to the second reagent aspirating position, when the reagent container rack holding the target reagent container is the second reagent container rack, based on the position information of the target reagent container obtained in step (b).

DETAILED DESCRIPTION OF THE PREFERRED EMBODIMENTS

Figure 1:
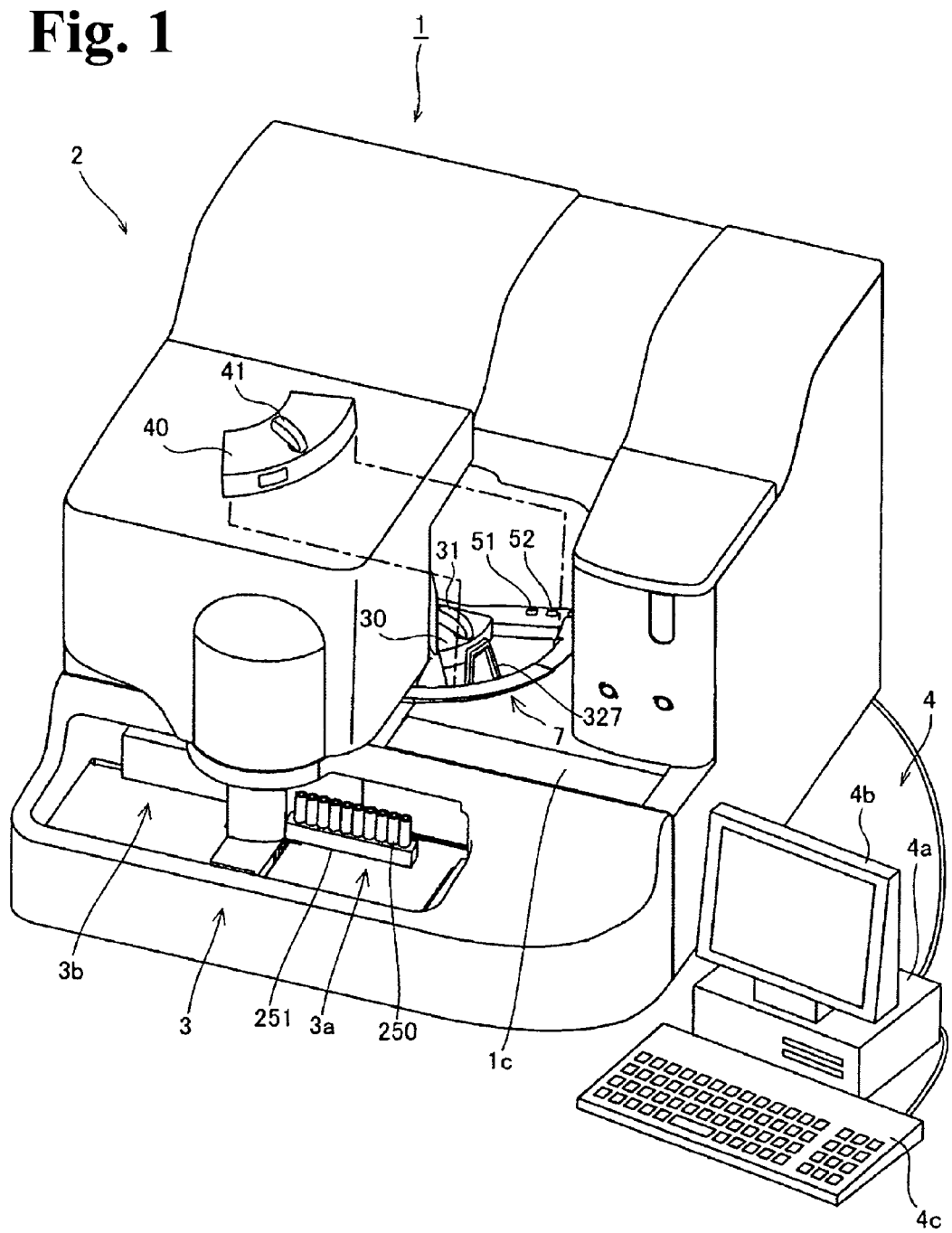
FIG. 1 is a perspective view showing an overall configuration of a sample analyzer according to one embodiment of the present invention.

The embodiments according to the present invention will now be described in detail with reference to the drawings.

A sample analyzer 1 is an apparatus for analyzing the amount or degree of activity of a specific substance related to coagulation and fibrolytic function of the blood by optically measuring the same, and uses blood plasma for the sample. As shown in FIGS. 1 to 5, the sample analyzer 1 is configured by a measurement mechanism unit 2, a sample conveyance mechanism unit 3 arranged on the front face side of the measurement mechanism unit 2, and a control device 4 electrically connected to the measurement mechanism unit 2.

The conveyance mechanism unit 3 has a function of conveying a rack 251 mounted with a plurality of (ten in the present embodiment) test tubes 250 which contains the sample to an aspirating position 2a (see FIG. 3) of the measurement mechanism unit 2 to supply the sample to the measurement mechanism unit 2.

The control device 4 comprises a personal computer 401 (PC), as shown in FIG. 1, and includes a control section 4a, a display 4b and a keyboard 4c. The control section 4a is adapted to transmit operation start signals of the measurement mechanism unit 2 and the conveyance mechanism unit 3 to a control section 501 of the measurement mechanism unit 2, to be hereinafter described, and to have a function to analyze optical information of the sample obtained by the measurement mechanism unit 2. The control section 4a is made up of CPU, ROM, RAM, or the like. The display 4b is provided to display analysis result etc. obtained by the control section 4a.

Figure 6:
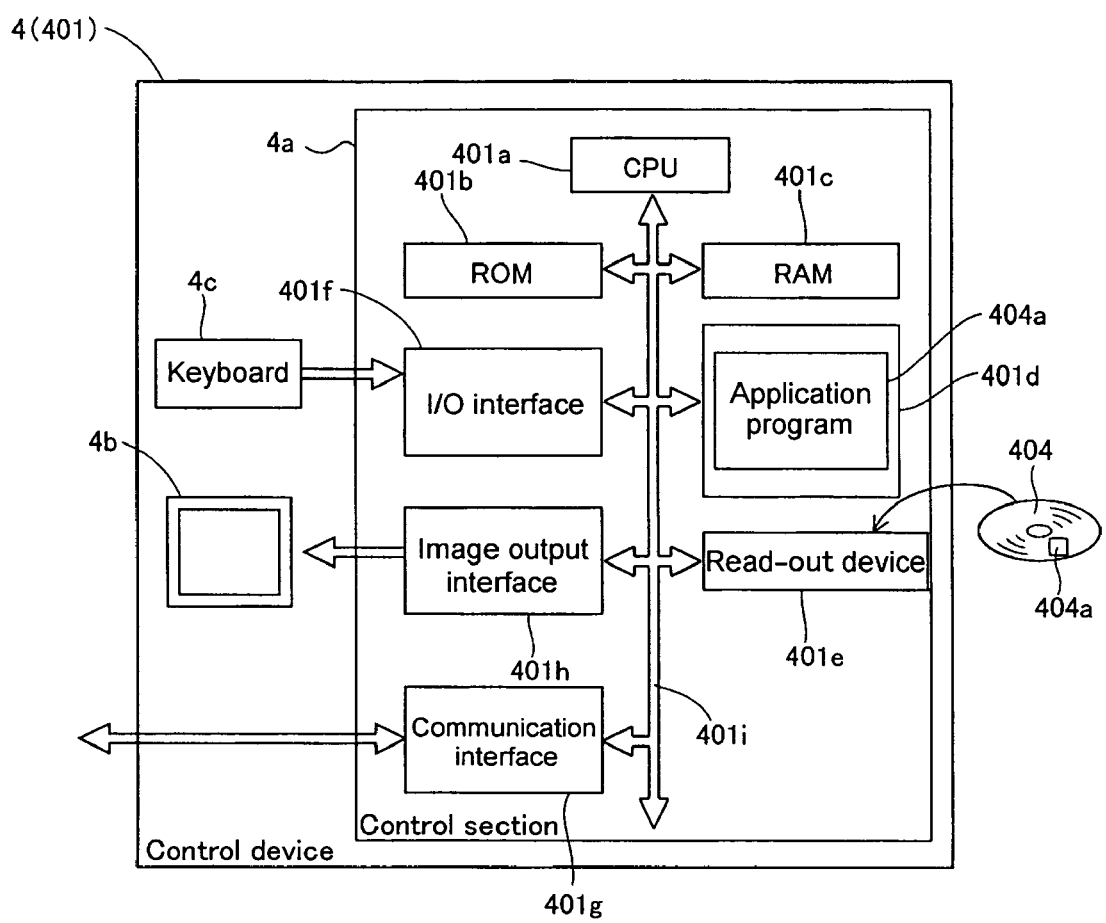
FIG. 6 is a block diagram showing a control device of the sample analyzer according to one embodiment of the present invention.

The configuration of the control device 4 will now be described in detail. As shown in FIG. 6, the control section 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. In the present embodiment, a table such as a reagent master, a reagent lot master, and a container master described hereinafter is stored in the hard disc 401d.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, so that the computer 401 can read out the application program from the portable recording medium 404, and install the application program 404a to the hard disc 401d.

The application program 404a may be not only provided by the portable recording medium 404, and may be but also provided through electrical communication line (wired or wireless) from external devices communicatably connected with the computer 401 through the electrical communication line. For instance, the application program 404a may be stored in the hard disc of the server computer on the internet, so that the computer 401 can access to the server computer to download the application program 404a and install the application program 404a to the hard disc 401d.

Operating system providing graphical interface environment such as Windows (registered trademark) manufactured and sold by US Microsoft Co. is installed in the hard disc 401d. In the following description, the application program 404a according to the present embodiment is assumed to be operating on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 can transmit and receive data with the measurement mechanism unit 2 using a predetermined communication protocol by means of the communication interface 401g.

The image output interface 401h is connected to the display 4b configured by LCD, CRT, or the like, and is configured to output an image signal corresponding to the image data provided by the CPU 401a to the display 4b. The display 4b displays the image (screen) according to the input image signal.

Figure 7:
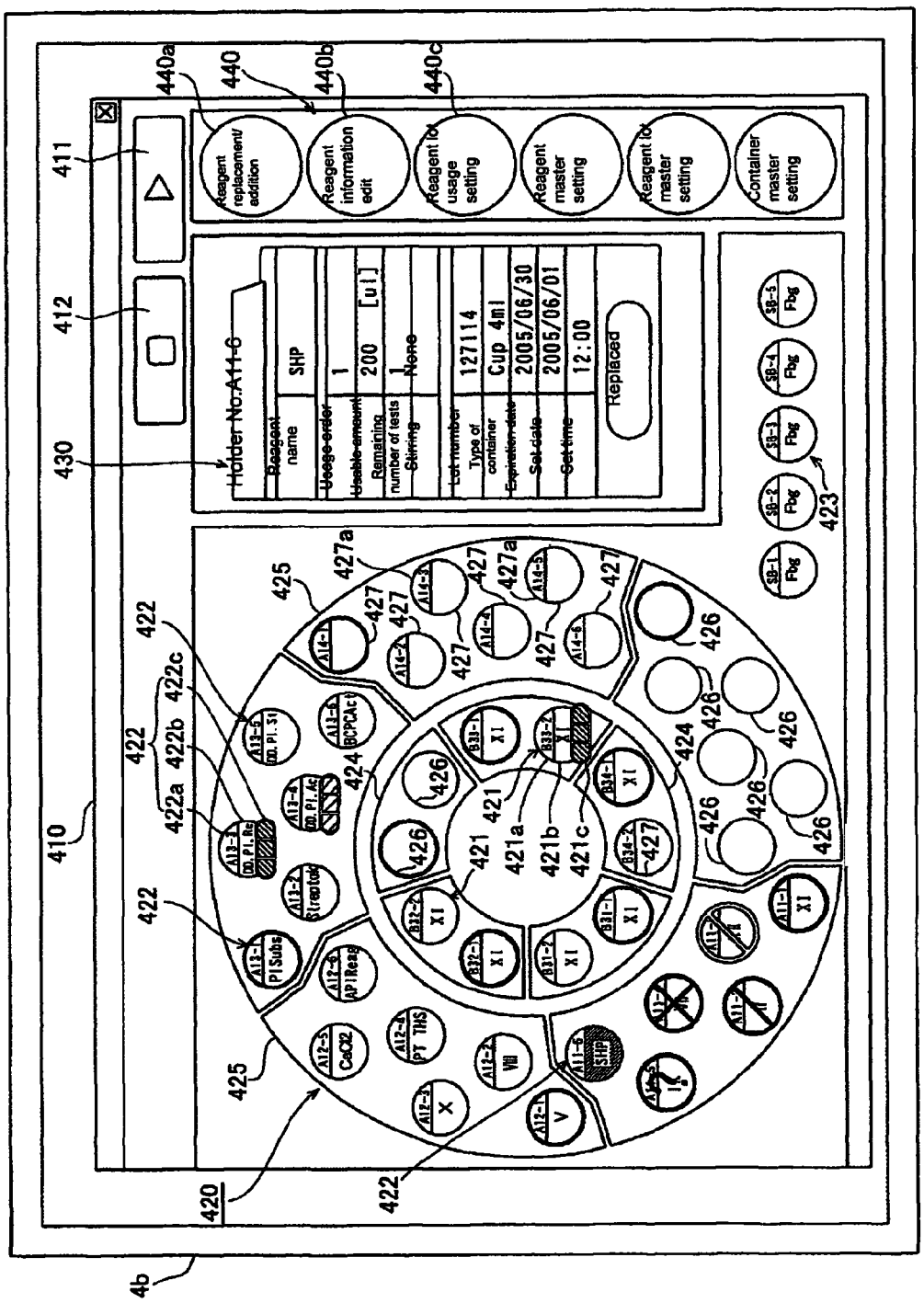
FIG. 7 is a view showing a reagent managing screen displayed on a display of a control device according to one embodiment of the present invention.

As shown in FIG. 7, in the present embodiment, the display 4b can display a reagent arrangement screen 410 that displays the arrangement of the reagents of a reagent storing section 6 described hereinafter. The reagent managing screen 410 includes a reagent arrangement displaying region 420, a reagent information displaying region 430, and a command displaying region 440. A measurement start button 411 for starting the measurement of the sample analyzer 1 and a measurement stop button 412 for stopping the measurement are arranged on the reagent arrangement screen 410. The display 4b has a touch panel function, so that the user can select or operate by directly touching the button etc. displayed on the reagent arrangement screen 410.

The reagent arrangement displaying region 420 includes a plurality of first reagent displaying regions 421 displaying the reagents arranged on a first reagent table 11, to be hereinafter described, and a plurality of second reagent displaying regions 422 displaying the reagents arranged on a second reagent table 12, to be hereinafter described. The first reagent displaying region 421 includes a position displaying part 421a for displaying the position of the reagent, a reagent name displaying part 421b for displaying the reagent name, and a remaining amount displaying part 421c for displaying the remaining amount of the reagent. Furthermore, the second reagent displaying region 422 includes a position displaying part 422a for displaying the position of the reagent, a reagent name displaying part 422b for displaying the reagent name, and a remaining amount displaying part 422c for displaying the remaining amount of the reagent. The positions of the reagents displayed on the position displaying parts 421a and 422a are displayed by reading barcodes 311b, 312b (see FIG. 8) of a first reagent container rack 310, to be hereinafter described, barcodes 321b to 326b (see FIG. 9) of a second reagent container rack 320, and barcodes 331b to 338b (see FIG. 13) of a third reagent container rack 330 with a reagent barcode reader 350. The reagent names displayed on the reagent name displaying parts 421b and 422b are displayed with reference to a list prepared separately based on the value read by the reagent barcode reader 350 from the barcode 300a of the reagent container 300. The remaining amounts of the reagent displayed on the remaining amount displaying parts 421c and 422c are displayed based on the values obtained from the type of container containing the reagent and the number of times that the reagent is aspirated.

The first reagent displaying region 421 is displayed while being divided into by twos for every region corresponding to five first reagent container racks 310 capable of holding two reagent containers 300 arranged on the first reagent table 11. The second reagent displaying reagent 422 is displayed while being divided into by sixes for every region corresponding to five second reagent container racks 320 capable of holding six reagent containers 300 arranged on the second reagent table 12. Although only a case where the second reagent container rack 320 is arranged on the reagent table 12 is shown in FIG. 7, if the third reagent container rack 330 capable of holding eight reagent containers 300 is arranged on the second reagent table 12, the second reagent displaying region 422 is displayed while being divided into eights for every region corresponding to the third reagent container rack 330. Accordingly, the reagent arrangement screen 410 allows checking of at which position of which reagent container rack (first reagent container rack 310, second reagent container rack 320, or third reagent container 330) of which reagent table (first reagent table 11 or second reagent table 12) the reagent is arranged.

Furthermore, when the first reagent container rack 310 (FIG. 8), the second reagent container rack 320 (FIG. 9), or the third reagent container rack 330 (FIG. 13) are not arranged on the first reagent table 11 or the second reagent table 12, nothing will be displayed on the first reagent displaying region 421 or the second reagent displaying region 422. If the first reagent container rack 310, the second reagent container rack 320, or the third reagent container 330 is arranged on the first reagent table 11 or the second reagent table 12, and the reagent container 300 to be held by the reagent container rack does not exist, the display is made only on the position displaying part 421a or the position displaying part 422a at the first reagent displaying region 421 or the second reagent displaying region 422. This will be hereinafter described in detail.

On the reagent information displaying region 430, attribute information (reagent name, usage order, usable remaining amount (usable amount), remaining number of tests, necessity of stirring, lot number, type of reagent container, expiration date of reagent, set date, set time etc.) and the holder number of the reagent specified in the first reagent displaying region 421 or the second reagent displaying region 422 are displayed. The user can determine the time to replace the reagent with the attribute information of the reagent.

The command displaying region 440 includes a replacement/addition instructing button 440a for instructing replacement and addition of the reagent, the edit button 440b for editing the reagent information, a reagent lot setting button 440c for manually inputting the reagent lot. In the present embodiment, when the replacement/addition instructing button 440a is selected with the reagent specified, the first reagent container rack 310, the second reagent container rack 320, or the third reagent container rack 330 holding the reagent container 300 which contains the specified reagent is moved to a retrieving position where it can be taken out from the sample analyzer 1. When addition of the reagent is performed, the replacement/addition instructing button 440a is selected with the first reagent displaying region 421 or the second reagent displaying region 422 not arranged with the reagent specified. The first reagent container rack 310, the second reagent container rack 320, or the third reagent container 330 which does not contain the reagent is thus moved to the retrieving position.

Figure 2:
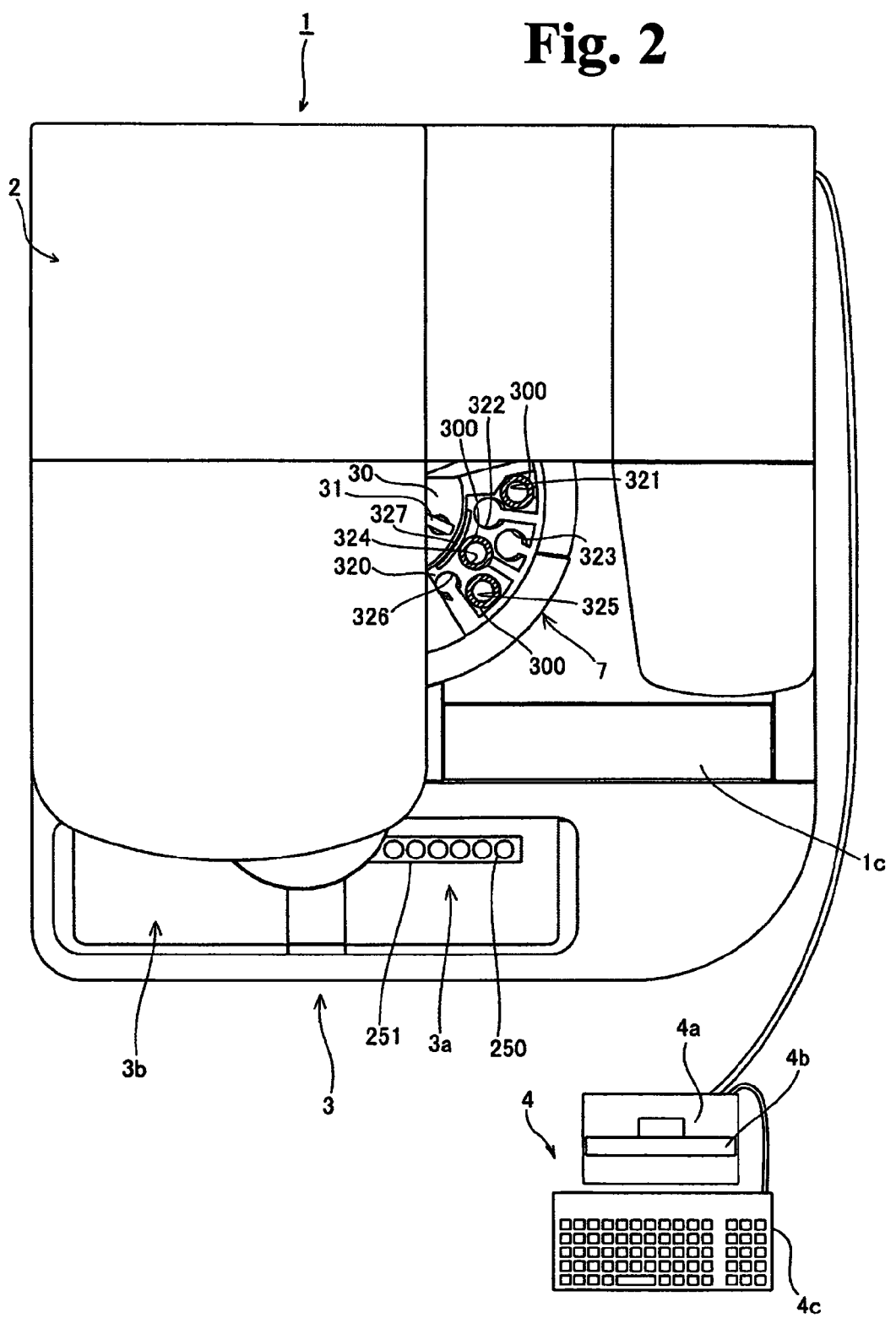
FIG. 2 is a plan view of the sample analyzer shown in FIG. 1.
Figure 3:
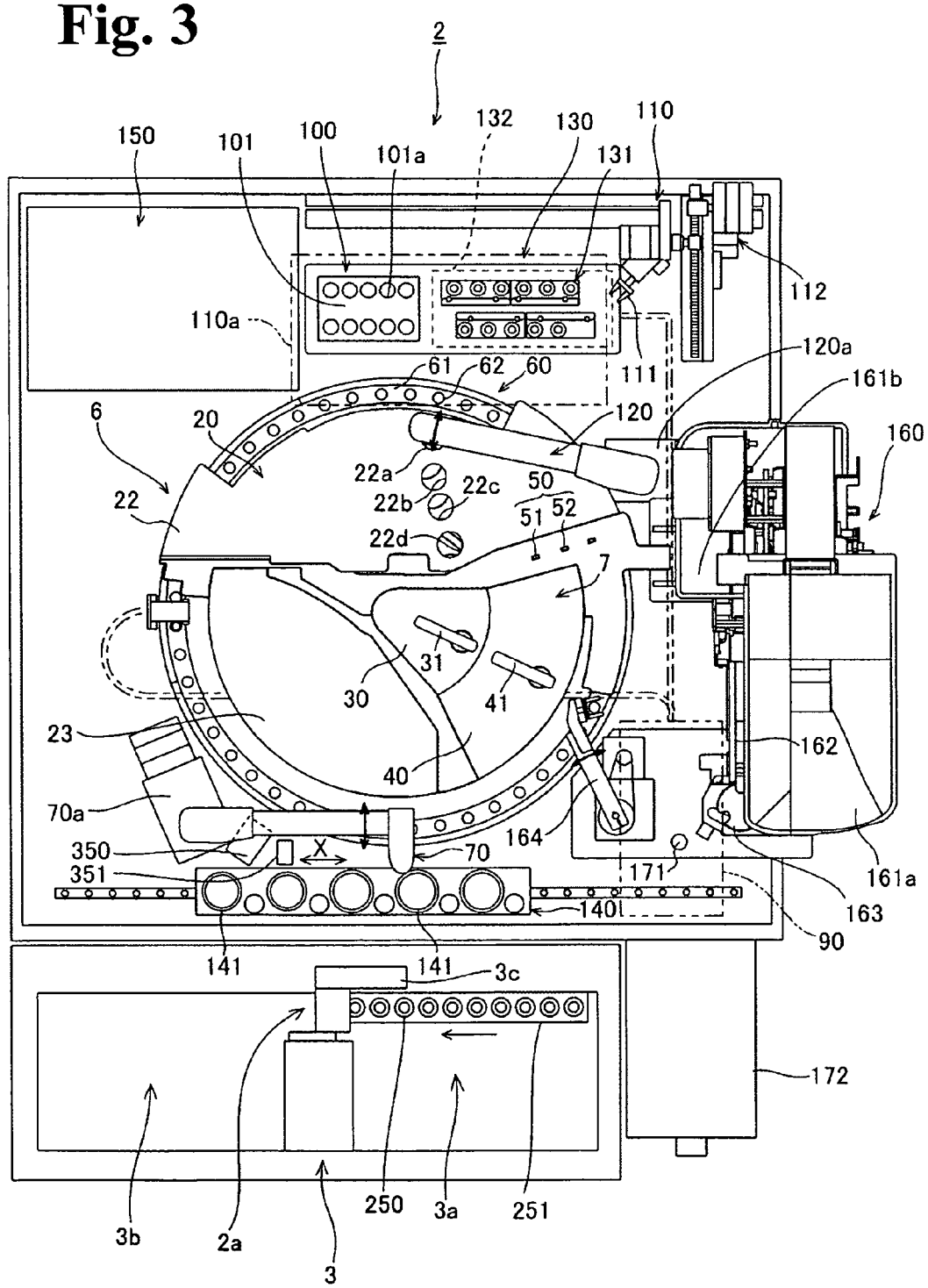
FIG. 3 is a plan view showing a measurement mechanism unit of the sample analyzer according to one embodiment of the present invention.

As shown in FIGS. 1 to 3, the conveyance mechanism unit 3 has a function of conveying a rack 251 mounted with a plurality of (ten in the present embodiment) test tubes 250 containing the sample to the aspirating position 2a (see FIG. 3) of the measurement mechanism unit 2 to supply the sample to the measurement mechanism unit 2. The conveyance mechanism unit 3 includes a rack set region 3a for setting the rack 251 in which the test tubes 250 containing non-processed sample are contained, and a rack accommodating region 3b for accommodating the rack 251 in which the test tubes 250 containing processed sample are contained.

The measurement mechanism unit 2 is configured to perform optical measurement on the sample supplied from the conveyance mechanism unit 3 to obtain optical information about the supplied sample. In the present embodiment, the optical measurement is performed on the sample dispensed into the cuvette 200 of the measurement mechanism unit 2 from the test tube 250 mounted on the rack 251 of the conveyance mechanism unit 3. As shown in FIG. 3, the measurement mechanism unit 2 includes a reagent storing section 6 for storing the reagent, and a reagent replacing section 7 for replacing or adding the reagent.

Figure 14:
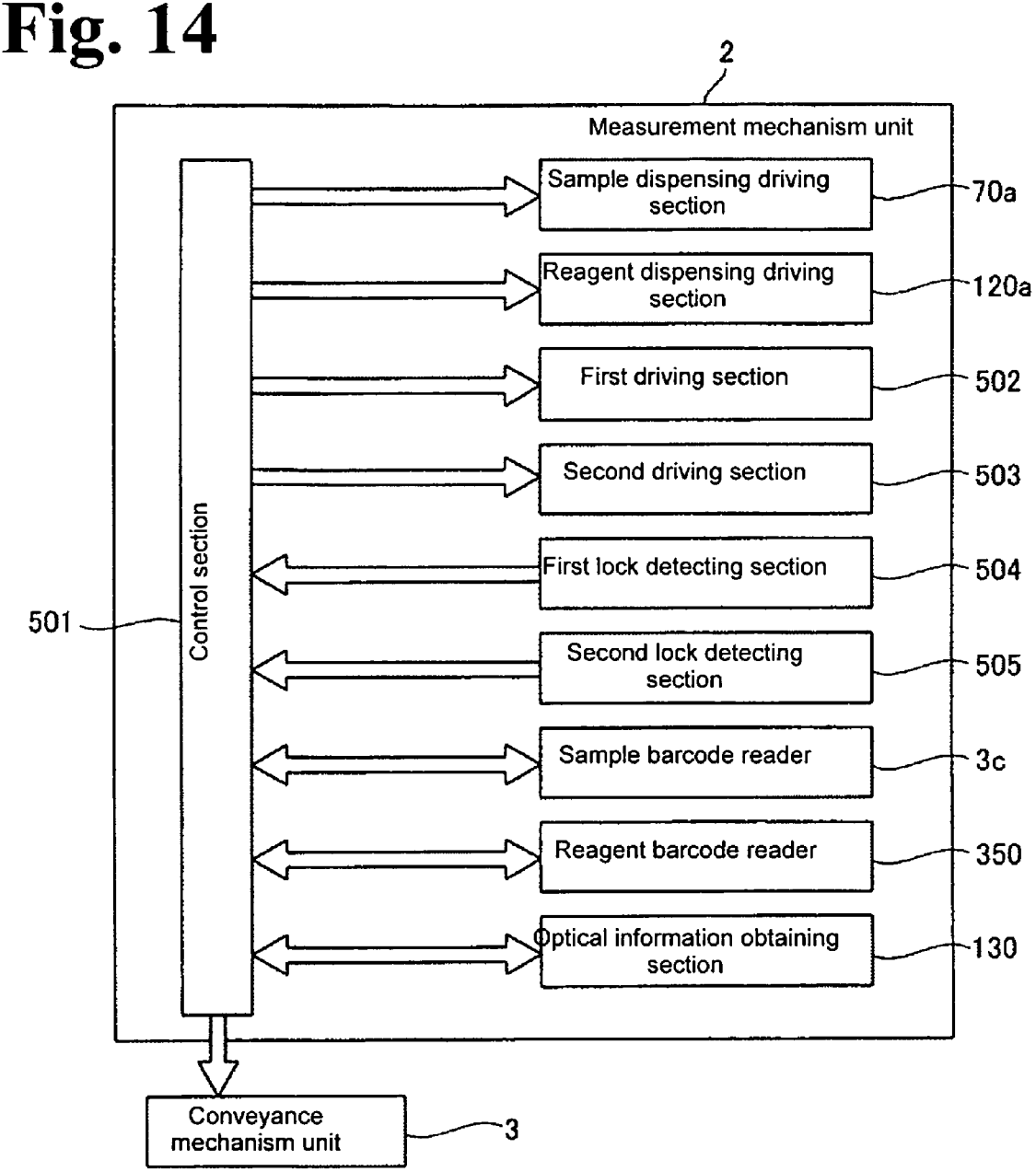
FIG. 14 is a block diagram of the sample analyzer according to one embodiment of the present invention.

As shown in FIG. 14, the measurement mechanism unit 2 includes a sample dispensing driving section 70a, a reagent dispensing driving section 120a, a first driving section 502, a second driving section 503, a first lock detecting section 504, a second lock detecting section 505, a reagent barcode reader 350, a sample barcode reader 3c, an optical information obtaining section 130, and a control section 501 electrically connected to the conveyance mechanism unit 3 and the like.

The sample dispensing driving section 70a includes a stepping motor 70b having a function of rotatably raising and lowering a sample dispensing arm 70 (see FIGS. 3 and 5), to be hereinafter described, a drive circuit (not shown) for driving the stepping motor 70b, and a pump (not shown) for aspirating and dispensing the sample.

The reagent dispensing driving section 120a includes a stepping motor 120b having a function of rotatably raising and lowering a reagent dispensing arm 120 (see FIGS. 3 and 5), to be hereinafter described, a drive circuit (not shown) for driving the stepping motor 120b, and a pump (not shown) for aspirating and dispensing the sample.

The first driving section 502 includes a first stepping motor (not shown) having a function of rotating the first reagent table 11 (see FIG. 5) and a drive circuit (not shown) for driving the first stepping motor. The first reagent table 11 rotates by an amount corresponding to the number of pulses of the drive pulse signal provided from the control section 501 to the first driving section 502, and then stops.

Similarly, the second driving section 503 includes a second stepping motor (not shown) having a function of rotating the second reagent table 12 (see FIG. 5) and a drive circuit (not shown) for driving the second stepping motor. The second reagent table 12 rotates by an amount corresponding to the number of pulses of the drive pulse signal provided from the control section 501 to the second driving section 503, and then stops.

The control section 501 counts the number of pulses of the provided drive pulse signal to determine the rotation movement amount of each reagent table 11, 12 from the origin positions of the first reagent table 11 and the second reagent table 12, and can control the rotation movement of each reagent table 11, 12.

The first lock detecting section 504 has a function of detecting the lock state of a first lid 30 (see FIG. 3) and transmitting a lock signal to the control section 501 when locked.

Similarly, the second lock detecting section 505 has a function of detecting the lock state of a second lid 40 (see FIG. 3) and transmitting a lock signal to the control section 501 when locked.

Figure 4:
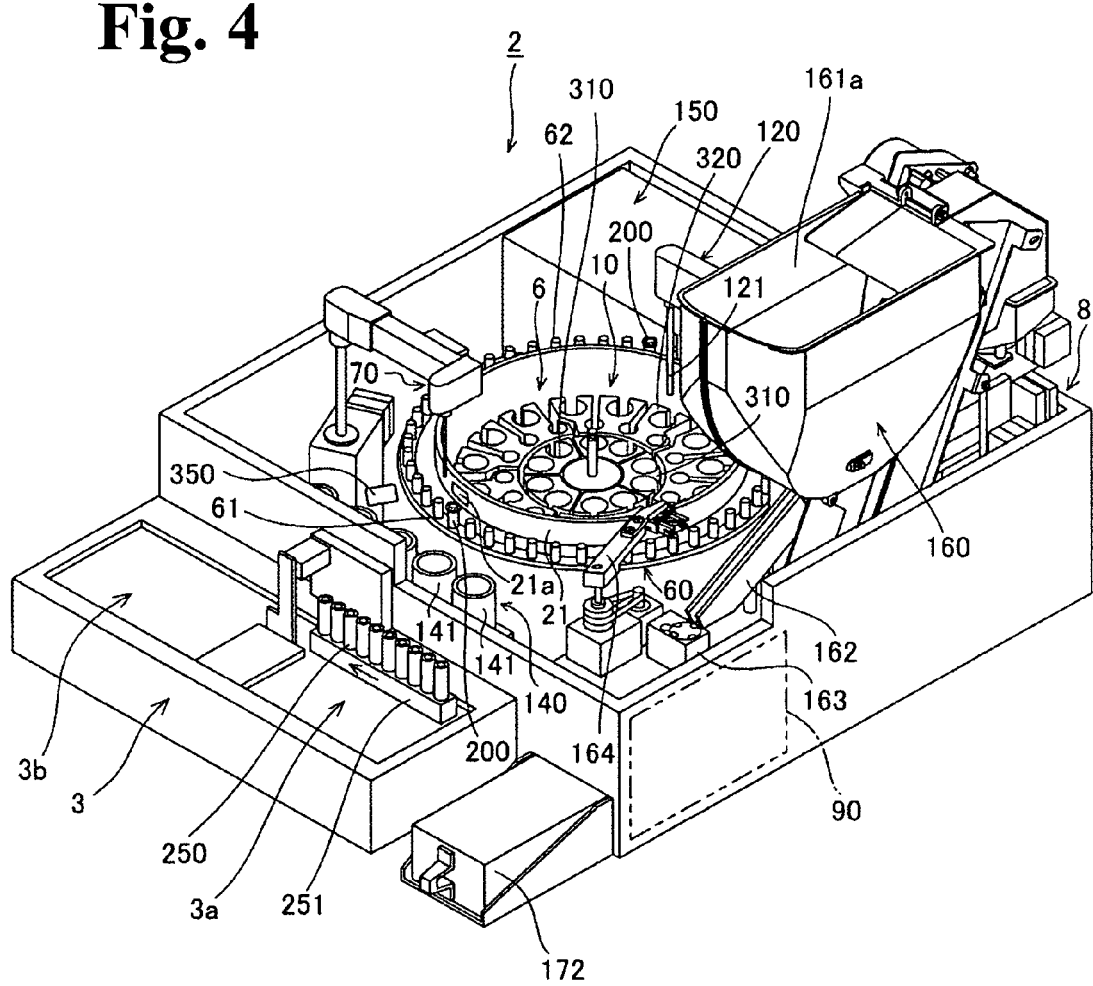
FIG. 4 is a perspective view showing the interior of the measurement mechanism unit and a reagent storing section of the sample analyzer according to one embodiment of the present invention.
Figure 5:
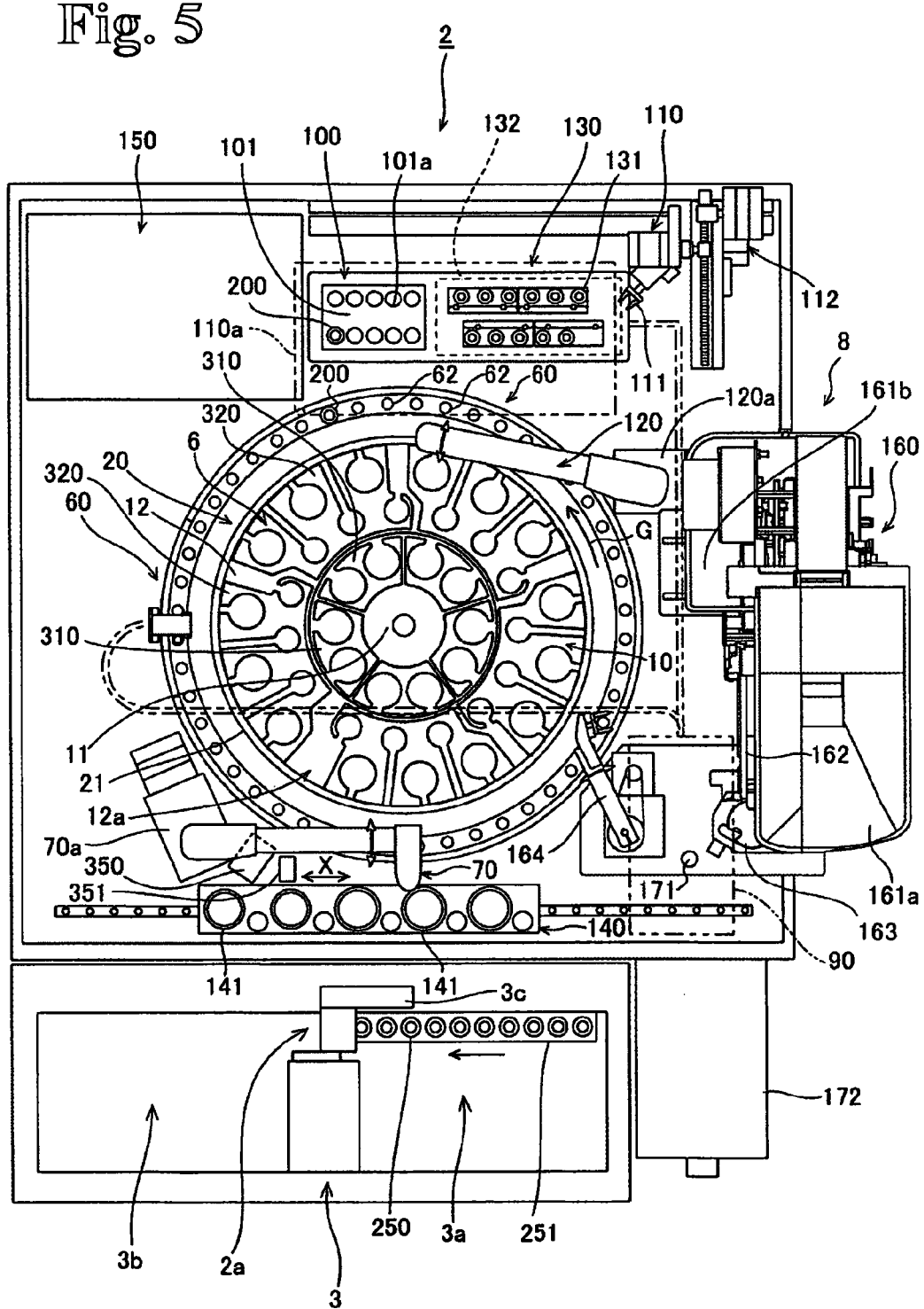
FIG. 5 is a plan view showing the interior of the measurement mechanism unit and the reagent storing section shown in FIG. 4.

The reagent barcode reader 350 has a function of reading each barcode on the first reagent table 11 and the second reagent table 12, and is arranged in the vicinity of the side surface 21 of the reagent storing section 6 at a predetermined distance from the reagent storing section 6 (see FIGS. 3 to 5). The reagent barcode reader 350 can transmit and receive data with the control section 501, and includes a drive circuit (not shown) for ON/OFF controlling the reagent barcode reader 350. The position of the reagent barcode reader 350 is always fixed.

The sample barcode reader 3c has a function of reading the barcode attached to the test tube 250 in which the sample mounted on the rack 251 conveyed by the conveyance mechanism unit 3 is contained, and is arranged in the vicinity of the aspirating position 2a of the measurement mechanism unit 2 described above so as to face the rack 251 conveyed by the conveyance mechanism unit 3 (see FIGS. 3 to 5). The sample barcode reader 3c can transmit and receive data with the control section 501, and also includes a drive circuit (not shown) for ON/OFF controlling the sample barcode reader 3c. The position of the sample barcode reader 3c is always fixed.

The optical information obtaining section 130 (see FIGS. 3 and 5) has a function of obtaining the optical information of the sample, and is configured to transmit and receive data with the control section 501. The details of the optical information obtaining section 130 will be hereinafter described in detail.

Figure 15:
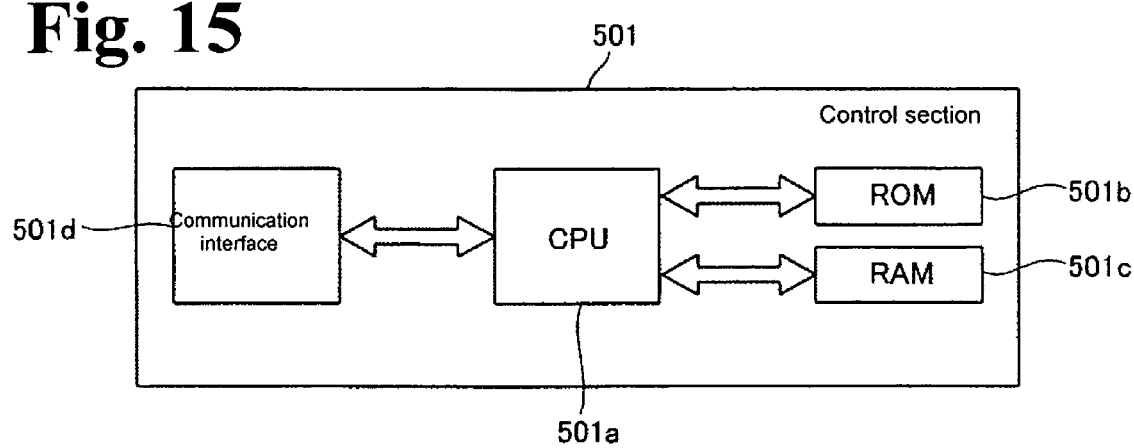
FIG. 15 is a block diagram of the control section of the measurement mechanism unit of the sample analyzer according to one embodiment of the present invention.

As shown in FIG. 15, the control section 501 is mainly configured by a CPU 501a, a ROM 501b, a RAM 501c, and a communication interface 501d.

The CPU 501a executes computer programs stored in the ROM 501b and the computer programs loaded in the RAM 501c. The ROM 501b is recorded with computer programs to be executed by the CPU 501a, data used for executing the computer program, and the like. The RAM 501c is used to read out the computer programs recorded on the ROM 501b. The RAM 501c is used as a work region of the CPU 501a when executing the computer programs.

The communication interface 501d is connected to the control device 4, and has a function of transmitting optical information of the sample to the control device 4 and receiving the signal from the control section 4a of the control device 4. The communication interface 501d has a function of transmitting commands from the CPU 501a for driving each section of the conveyance mechanism unit 3 and the measurement mechanism unit 2.

As shown in FIG. 3, the measurement mechanism unit 2 includes the reagent storing section 6 for storing the reagent and the reagent replacing section 7 for replacing or adding the reagent.

The reagent storing section 6 is arranged to refrigerate the reagent container 300 containing the reagent to be added to the sample in the cuvette 200 at low temperature (about 10° C.) and to convey the reagent container 300 in the rotating direction. The alteration of the reagent is suppressed by storing the reagent at low temperature. The reagent storing section 6 includes a regent conveying part 10 (see FIGS. 4 and 5) for holding and rotation conveying the reagent and an outer wall 20 (see FIG. 3) arranged so as to cover the periphery and the upper side of the reagent conveying part 10, as shown in FIGS. 3 to 5. The reagent conveying part 10 for holding the reagent is arranged in the refrigerating region formed by the outer wall part 20, and the first lid 30 and the second lid 40 of the reagent replacing section 7, to be hereinafter described.

As shown in FIG. 5, the reagent conveying part 10 includes the first reagent table 11 of circular shape, and the second reagent table 12 of circular ring shape arranged concentrically with respect to the first reagent table 11 on the outer side of the first reagent table 11 of circular shape. The first reagent table 11 is configured so that the first reagent container rack 310 for holding the reagent container 300 can be removably arranged, and the second reagent table 12 is configured so that the second reagent container rack 320 and the third reagent container rack 330 for holding the reagent container 300 can be removably arranged. The outer wall part 20 is configured by a side face 21 (see FIG. 4), an upper face 22 (see FIG. 3) fixed to the side face 21, and a detachable lid 23 (see FIG. 3). The reagent barcode reader 350 is arranged in the vicinity of the side face 21 (see FIG. 4) of the reagent storing section 6 at a predetermined distance with the reagent storing section 6.

The first reagent table 11 and the second reagent table 12 are respectively configured so as to be rotatable both in the clockwise direction and in the counterclockwise direction, and so that each table is rotatable independent from each other. The first reagent container rack 310, the second reagent container rack 320, and the third reagent container rack 330 for holding the reagent container 300 containing the reagent are respectively conveyed in the rotating direction by the first reagent table 11 and the second reagent table 12. The reagent to be dispensed can be arranged close to the reagent dispensing arm 120 when the reagent dispensing arm 120 dispenses the reagent by conveying the reagent container 300 in the rotating direction.

Furthermore, a heat insulation material (not shown) is attached to the side face 21 of the outer wall part 20 so that cooled air in the reagent storing section 6 (refrigerating region) does not escape. As shown in FIG. 4, a shutter 21a that can be opened and closed is arranged at a position facing the reagent barcode reader 350 of the side face 21 of the outer wall part 20. The shutter 21a is configured to open only when reading the barcodes of the reagent container 300, the first reagent container rack 310, the second reagent container rack 320, and the third reagent container rack 330 with the reagent barcode reader 350. The cooled air in the reagent storing section 6 (refrigerating region) is thereby prevented from escaping to the outside.

As shown in FIG. 3, the upper face 22 of the outer wall part 20 includes four holes 22a, 22b, 22c and 22d. The aspiration of the reagent stored in the reagent storing section 6 is performed by the reagent dispensing arm 120 through the four holes 22a, 22b, 22c, and 22d. The holes 22a to 22c are positioned above the reagent container 300 held in the second reagent container rack 320 and the third reagent container rack 330. The reagent is aspirated from the reagent container 300 held in the second reagent container rack 320 and the third reagent container rack 330 through the holes 22a to 22c. The hole 22d is positioned above the reagent container 300 held in the first reagent container rack 310. The reagent is aspirated from the reagent container 300 held in the first reagent container rack 310 through the hole 22d.

A semicircular opening is formed in the reagent storing section 6 (refrigerating region) by detaching the lid 23 with the first lid 30 and the second lid 40 described hereinafter. When starting the measurement in the sample analyzer 1, the first reagent container rack 310, the second reagent container rack 320, and the third reagent container rack 330 are arranged in the reagent storing section 6 through such opening.

Figure 8:
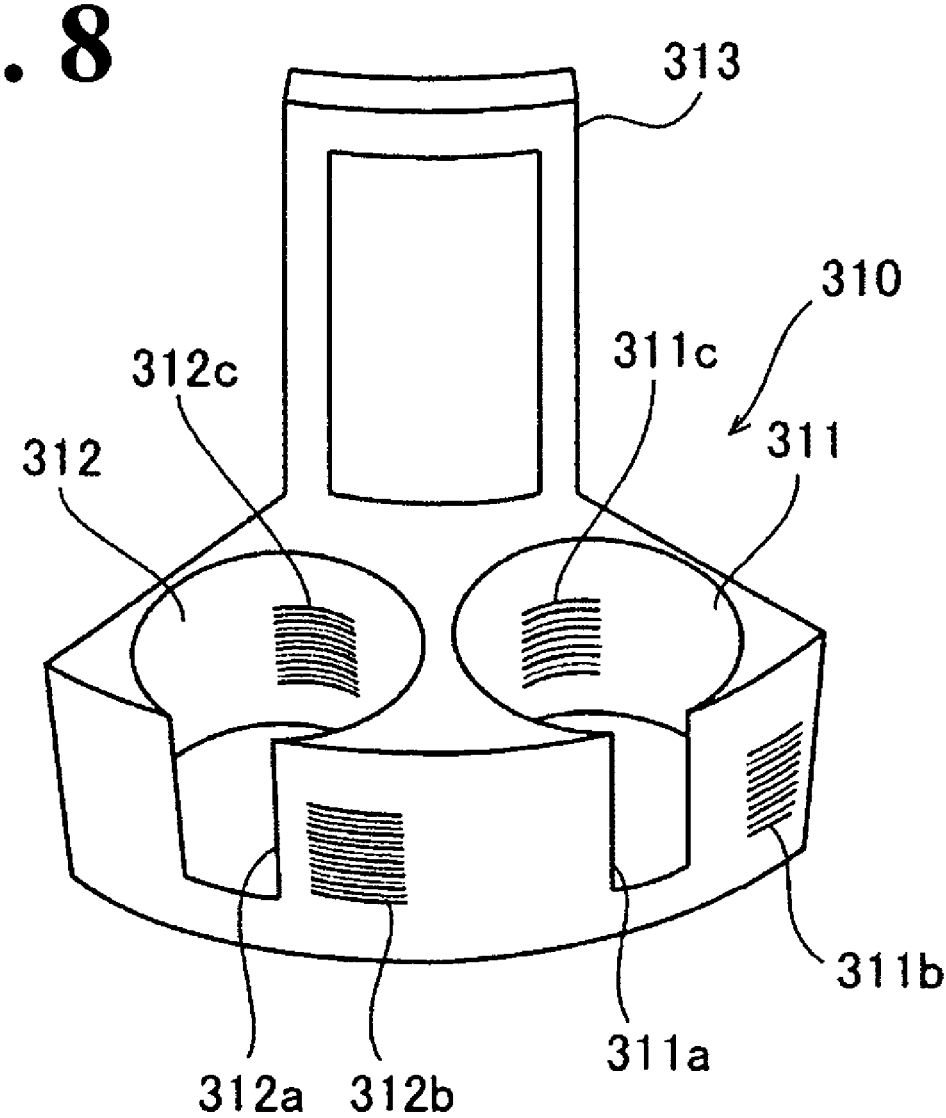
FIG. 8 is a perspective view showing a first reagent container rack according to one embodiment.
Figure 10:
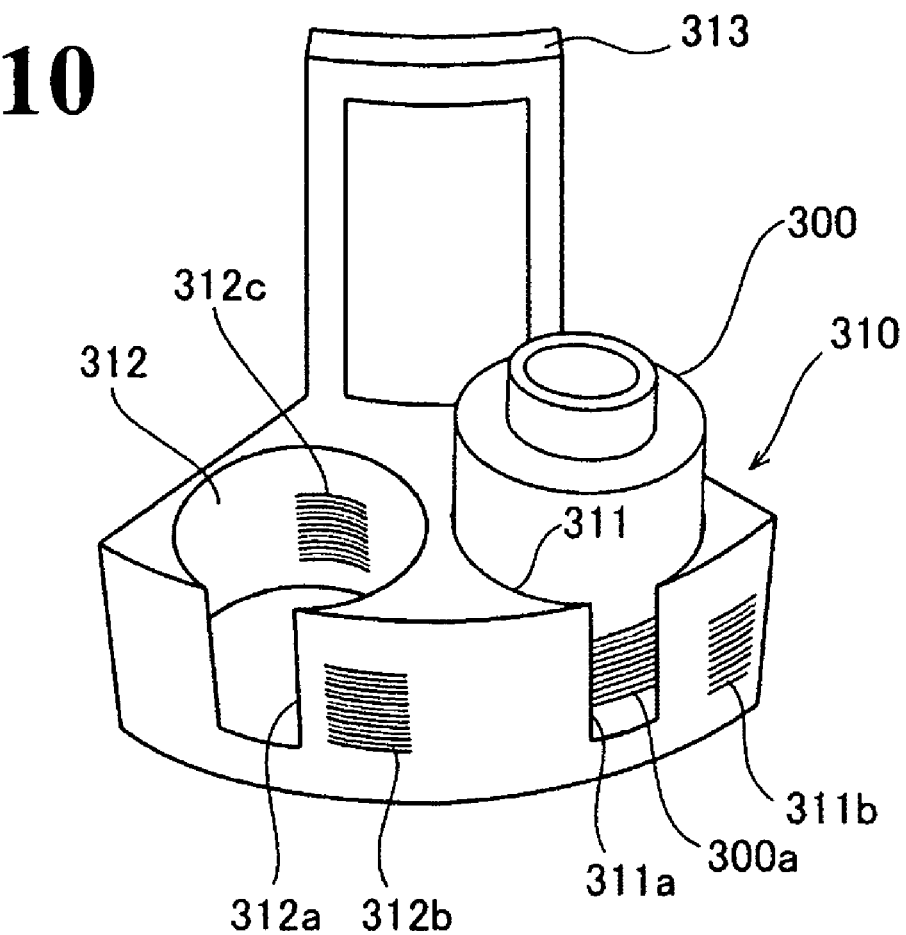
FIG. 10 is a perspective view showing a state in which a regent container is held in the first reagent container rack shown in FIG. 8.

As shown in FIG. 5, five first reagent container racks 310 can be arranged in the first reagent table 11. The reagent containers 300 are arranged in a circular ring shape in the five first reagent container racks 310. As shown in FIGS. 8 and 10, the first reagent container rack 310 includes two holders 310 and 312 for holding the reagent container 300, cut-out parts 311a and 312a respectively arranged on the front face side of the holders 311 and 312, and one gripping part 313 arranged so as to project upward. Moreover, as shown in FIG. 8, the holders 311 and 312 are formed into a circular shape in plan view, and are able to hold the reagent container 300 when the regent container 300 of cylindrical shape is inserted thereto. The reagent container 300 having an outer diameter smaller than the inner diameter of the holder 311 or 312 can be held by the holder 311 or 312 by attaching an adapter (not shown) to the holder 311 or 312. Barcodes 311b and 312b are respectively arranged on the front face side of the outer surface of the holders 311 and 312, and barcodes 311c and 312c are respectively arranged on the inner surface of the holders 311 and 312.

The two holders 311 and 312 can hold a plurality of reagent containers 300 containing various reagents to be added when preparing measurement sample from a sample one by one. That is, a maximum of ten ($2^\ast 5=10$) of reagent containers 300 can be arranged on the first reagent table 11. Each cut-out part 311a and 312a is arranged to read the barcodes 311c and 312c with the reagent barcode reader 350 (see FIG. 5). The gripping part 313 is gripped when taking out the first reagent container rack 310 from the reagent storing section 6.

Each barcode 311b and 312b includes holder number information for identifying the position of the holders 311 and 312. The barcodes 311c and 312c include information (no reagent container information) indicating that the reagent container 300 held by the holders 311 and 312 does not exist. Furthermore, the barcode 300a of the reagent container 300 includes information for specifying the detailed information (information of reagent name, type of reagent container, lot number, expiration date of reagent etc.) of the reagent contained in the reagent container 300.

If the reagent container 300 is held in the holder 311, the barcode 311c is not read and the barcode 300a of the reagent container 300 is read. That is, if the barcode 300a is read after the barcode 311b is read with the barcode reader 350, the control section 4a is configured to recognize that the reagent having the reagent information of the barcode 300a is held in the holder 311. In the reagent arrangement displaying region 420 of the reagent managing screen 410, the first reagent mark 421 is displayed at a position corresponding to the holder 311. If the barcode 311c is read after the barcode 311b is read by the barcode reader 350, the control section 4a is configured to recognize that the reagent container 300 being held at the holder 311 does not exist. In the reagent arrangement displaying region 420 of the reagent managing screen 410, the reagent non-arranged mark 427 is displayed at the position corresponding to the holder 311. If neither the barcode 300a or the barcode 311c is read after the barcode 311b is read by the barcode reader 350 (when reagent container 300 is facing the side), the control section 4a is configured to recognize a reading error and that a barcode reading error mark E indicating that reading has failed is displayed on the display 4b. If the first reagent container rack itself is not arranged in the first reagent table 11, the reagent barcode reader 350 does not read the barcodes 311b, 312b, 311c, 312c of the first reagent container rack 310 and the barcode 300a of the reagent container 300. Thus, in the reagent arrangement displaying region 420 of the reagent managing screen 410, the rack non-arranged mark 426 is displayed on the first rack mark 424 corresponding to the portion not arranged with the first reagent container rack 310.

Figure 9:
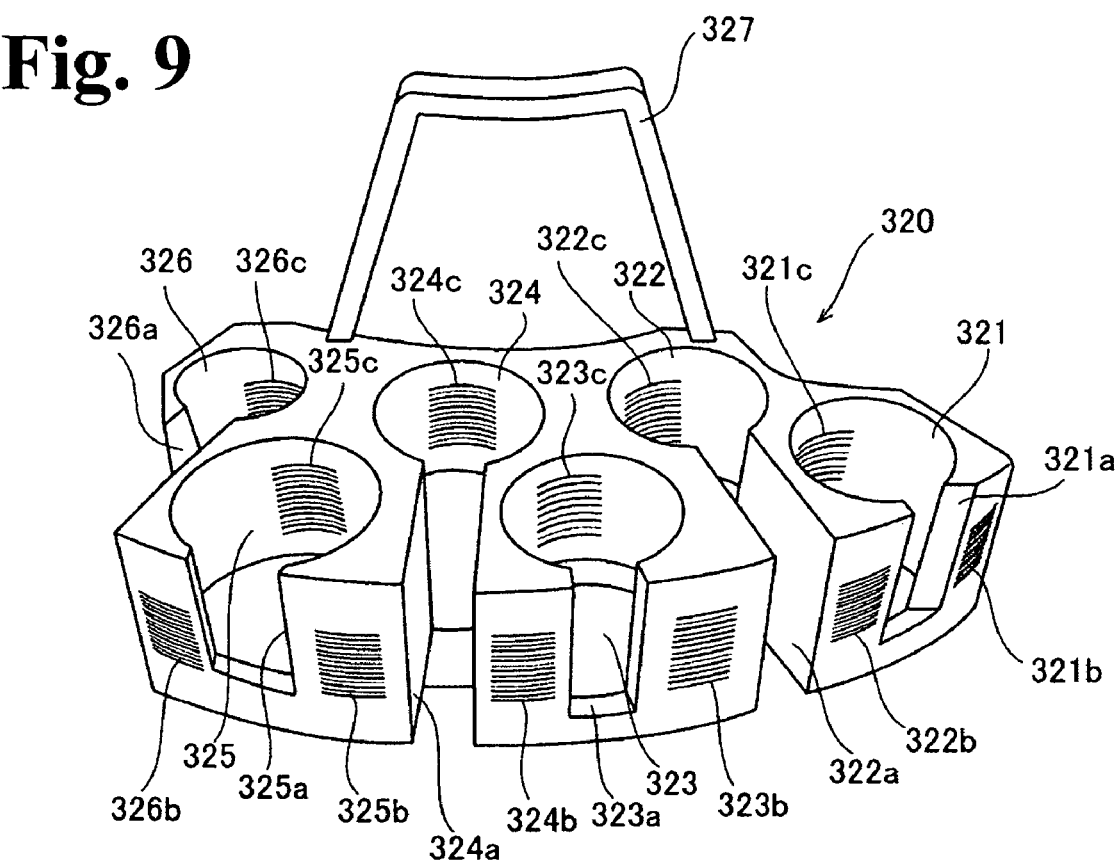
FIG. 9 is a perspective view showing a second reagent container rack according to one embodiment.
Figure 11:
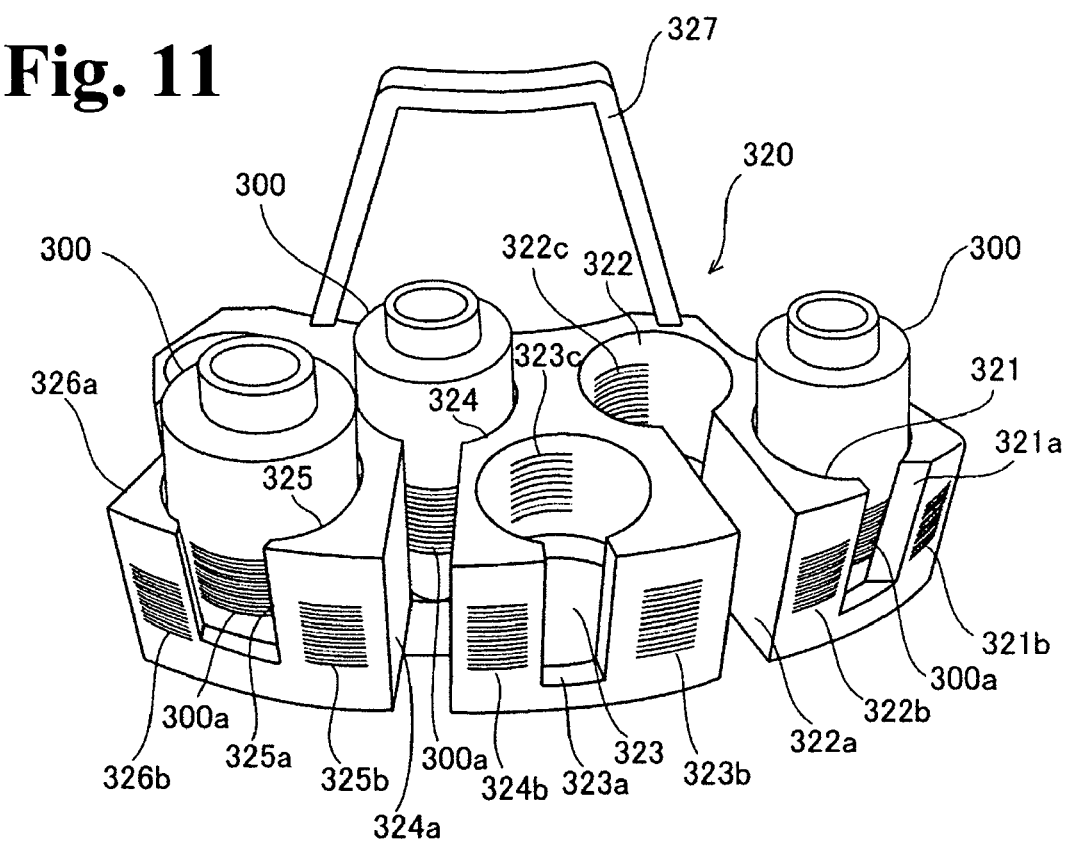
FIG. 11 is a perspective view showing a state in which the regent container is held in the second reagent container rack shown in FIG. 9.
Figure 12:
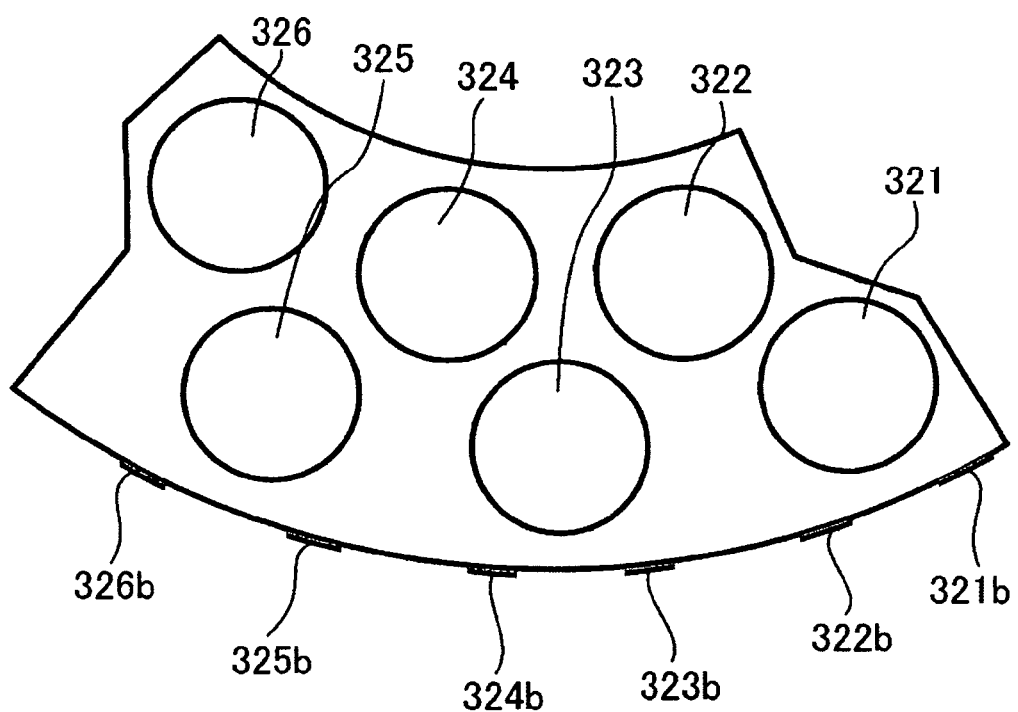
FIG. 12 is a schematic view of the second reagent container rack shown in FIG. 9 of rack type 1.

As shown in FIG. 5, five second reagent container racks 320 can be arranged in the second reagent table 12. The third reagent container rack 330 (FIG. 13) other than the second reagent container rack 320 is also arranged in the second reagent table 12. Since the outer shape of the second reagent container rack 320 and the outer shape of the third reagent container rack 330 are the same, five third reagent container racks 330 can also be arranged in the second reagent table 12, although not shown. The reagent containers 300 are arranged in a circular ring shape in the reagent container racks 320 and 330. One of the five gaps of the second reagent container rack 320 or the third reagent container rack 330 adjacent to each other has a spacing larger than the spacing of the other four gaps. The barcodes 311b and 312b of the first reagent container rack 310 arranged in the first reagent table 11 positioned on the inner side of the second reagent table 12 and the barcode 300a of the reagent container 300 held by the first reagent container rack 310 are read by the reagent barcode reader 350 positioned exterior to the reagent storing section 6 by way of a gap 12a having the large spacing. As shown in FIGS. 9, 11, and 12, the second reagent container rack 320 includes six holders 321 to 326 for holding the reagent container 300, cut-out parts 321a to 326a respectively arranged on the front face side of the holders 321 to 326, and one gripping part 327 arranged so as to project upward. Moreover, the holders 321 to 326 of the second reagent container rack 320 are formed into a circular shape in plan view, similar to the first reagent container rack 310, and can hold the reagent container 300 when the regent container 300 of cylindrical shape is inserted thereto. The reagent same as the reagent arranged in the first reagent container rack 310 can be arranged in the second reagent container rack 320.

Barcodes 321b and 322b are respectively arranged on both sides of the cut-out part 321a on the front column side of the second reagent container rack 320. Similarly, barcodes 323b and 324b as well as barcodes 325b and 326b are respectively arranged on both sides of the cut-put part 323a and on both sides of the cut-out part 325a. Barcodes 321c to 326c are respectively arranged on the inner surface of the holders 321 to 326.

Each barcode 321b to 326b includes holder number information for identifying the position of the holders 321 to 326. The barcodes 321c and 326c include information (no reagent container information) indicating that the reagent container 300 held by the holders 321 to 326 does not exist.

Figure 13:
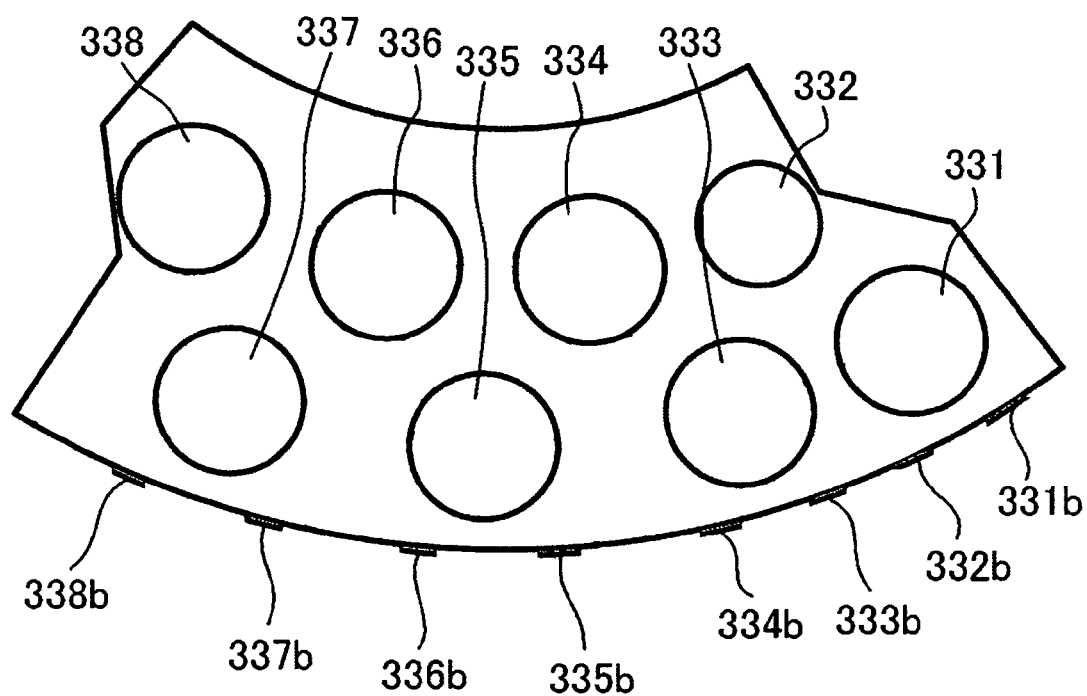
FIG. 13 is a schematic view of a third reagent container rack of rack type 2.

Furthermore, as shown in FIG. 13, the third reagent container rack 330 includes eight holders 331 to 338 for holding the reagent container 300, and barcodes 331b to 338b are arranged on both sides of the cut-out parts (not shown) respectively arranged on the front surface side of the holders 331 to 338. The barcodes 331b to 338b respectively contain holder number information for identifying the position of the holders 331 to 338.

Furthermore, the reagent information or no reagent container information read by the reagent barcode reader 350 are stored in a hard disc 401d of the control section 4a in correspondence to the holder number information. The information stored in the hard disc 401d is reflected on the reagent managing screen 410 of the display 4b by the control section 4a of the control device 4.

The barcodes 311b, 312b, 321b to 326b, and 331b to 338b show four digit values. The first digit takes a value of "A" or "B", where "A" indicates that the reagent container 300 is arranged in the second reagent table 12, and "B" indicates that the reagent container 300 is arranged in the first reagent table 11. The second digit takes a value between "1" to "3", where "1" indicates that the type of the relevant reagent container rack is the type of the second reagent container rack 320, "2" indicates that the type of the relevant reagent container rack is the type of the third reagent container rack 330, and "3" indicates that the type of the relevant reagent container rack is the type of the first reagent container rack 310. The third digit takes a value between "0" to "9" and indicates the number of the first reagent container rack 310, the second reagent container rack 320, or the third reagent container rack 330. The fourth digit takes a value of "1" or "2" in the barcodes 311b and 312b of the first reagent container rack 310, where "1" and "2" indicates the holder 311 and 312, respectively. The fourth digit takes a value between "1" and "6" in the barcodes 321b to 326b of the second reagent container rack 320, where "1" to "6" respectively indicates the holders 321 to 326. The fourth digit takes a value between "1" and "8" in the barcodes 331b to 338b of the third reagent container rack 330, where "1" to "8" respectively indicates the holders 331 to 338. The values of the barcodes (barcodes 311b, 312b, 321b to 326b, and 331b to 338b) are reflected on the position displaying part 421a of the first reagent mark 421, the position displaying part 422a of the second reagent mark 422, or the position displaying part 427a of the reagent non-arranged mark 427 of the reagent managing screen 410, as shown in FIG. 7. For example, if the value of the barcode is "A11-6", this represents the sixth holder (holder 326) of the second reagent container rack 320 of rack number 1 or the rack (second reagent container rack 320) that can be arranged in the second reagent table 12 and that corresponds to "1" of the three types. That is, the first three digits of the four digit values specify the reagent container rack, and the last one digit specifies the position of the reagent in the reagent container rack.

The reagent name of the detailed information is reflected on the reagent name displaying parts 421b and 422b of the first reagent mark 421 and the second reagent mark 422 of the reagent managing screen 410. The no reagent container information is reflected to the reagent non-arranged mark 427. That is, as shown in FIG. 7, the reagent name is displayed on the reagent name displaying part 421b or 422b if the reagent is arranged, and nothing will be displayed on the reagent name displaying part 421b or 422b if the reagent is not arranged. For example, the reagent name "CaC12" is arranged in the reagent position "A12-5", and the reagent is not arranged in the reagent position "A14-2".

As shown in FIGS. 1 and 2, the reagent replacing section 7 is arranged in the vicinity of the central part of the sample analyzer 1. In the present embodiment, the reagent replacing section 7 includes detachable first lid 30 and second lid 40 including a lock mechanisms 31 and 41, respectively, and a notifying part 50 for notifying the conveyance state of the first reagent table 11 and the second reagent table 12 to the user, as shown in FIG. 3.

The first lid 30 is adapted so as to be detached when replacing the reagent container 300 arranged in the first reagent table 11 (first reagent container rack 310). The lock mechanism 31 of the first lid 30 is arranged to lock the first lid 30 so as not to detach in time of normal use or after replacement or addition of the reagent is finished and to have the control section 4a recognize that replacement or addition of the reagent in the first reagent table 11 is finished.

The second lid 40 is adapted so as to be detached when replacing the reagent container 300 arranged in the second reagent table 12 (second reagent container rack 320). The lock mechanism 41 of the second lid 40 is arranged to lock the second lid 40 so as not to detach in time of normal use or after replacement or addition of the reagent is finished and to have the control section 4a recognize that replacement or addition of the reagent in the second reagent table 12 is finished.

The notifying part 50 includes two LED indicators 51 and 52. As shown in FIGS. 1 and 3, the two LED indicators 51 and 52 are arranged in the vicinity of the second lid 40, and are visible by the user from outside the sample analyzer 1. The LED indicators 51 and 52 can emit a blue or red light.

The LED indicator 51 has a function of notifying the user that the first reagent container rack 310 corresponding to the reagent of the first reagent table 11 specified by the user in the reagent managing screen 410 has moved to a retrieving position (below the first lid 30) where the reagent can be replaced. Specifically, the LED indicator 51 is configured to emit a red light while the first reagent table 11 is rotatably moving, and to emit a blue light when the first reagent container rack 310 corresponding to the reagent of the specified first reagent table 11 is moved to the retrieving position and stopped. Thus the timing of detaching the first lid 30 to replace or add the reagent can be notified to the user.

The LED indicator 52 has a function of notifying to the user that the second reagent container rack 320 corresponding to the reagent of the second reagent table 12 specified by the user in the reagent managing screen 410 has moved to a retrieving position (below the second lid 40) where the reagent can be replaced. Similar to the LED indicator 51, the LED indicator 52 is configured to emit a red light while the second reagent table 12 is rotatably moving, and to emit a blue light when the second reagent container rack 320 corresponding to the reagent of the specified second reagent table 12 is moved to the retrieving position and stopped.

The sample analyzer 1 is configured such that the reading of the barcode 300a of all the reagent containers 300 held in the first reagent container rack 310 or the second reagent container rack 320 for holding the replaced reagent is automatically performed after the user locks the first lid 30 or the second lid 40 when the replacement or addition of the reagent is finished. Thus, even when reagents other than the specified reagent contained in the same first reagent container rack 310 or the second reagent container rack 320 is replaced in addition to the specified reagent when one reagent is specified and the replacement of the reagent is instructed, the arrangement of the reagents after the replacement is correctly reflected on the reagent managing screen 410.

Furthermore, as shown in FIGS. 3 to 5, the measurement mechanism unit 2 includes a cuvette conveying section 60, the sample dispensing arm 70, a lamp unit 90, a warming section 100, a cuvette transporting section 110, the reagent dispensing arm 120, the optical information obtaining section 130, the urgent sample setting section 140, a fluid section 150, and a cuvette supply mechanism section 160.

The cuvette conveying section 60 has a function of conveying the cuvette 200 to each section of the sample analyzer 1. The cuvette conveying section 60 includes a cuvette conveying table 61 of circular ring shape arranged on the outer side of the second reagent table 12 of circular ring shape, and a plurality of cylindrical shaped cuvette holders 62 arranged at a predetermined interval along the circumferential direction on the cuvette conveying table 61. The cuvette holder 62 is arranged to hold the cuvette 200 one by one. The sample contained in the test tube 250 of the conveyance mechanism unit 3 and the reagent stored in the reagent storing section 6 are dispensed into the cuvette 200 (see FIG. 5) held in the cuvette holder 62 of the cuvette conveying table 61 to prepare the measurement sample.

The sample dispensing arm 70 has a function of aspirating the sample contained in the test tube 250 conveyed to the aspirating position 2a by the conveyance mechanism unit 3, and dispensing the aspirated sample into the cuvette 200 held by the cuvette holder 62 of the cuvette conveying table 61.

The warming section 100 includes a plate 101 that can be heat-retained, and is arranged with ten concave shaped cuvette holders 101a. Each cuvette holder 101a is capable of holding one cuvette 200, and has a function of warming the sample in the cuvette 200 to about 37° C. by holding the cuvette 200 dispensed with the sample for a few minutes in the cuvette holder 101a. The sample warmed by the warming section 100 is dispensed with reagent and subjected to measurement within a constant time after warming is finished. The alteration of the sample, and the measurement sample prepared from the sample and the reagent is suppressed, and stabilizes the measurement result.

The cuvette transporting section 110 is arranged to transport the cuvette 200 among the cuvette conveying section 60, the warming section 100, and the optical information obtaining section 130. The cuvette conveying section 110 includes a transport catcher part 111 for gripping the cuvette 200 and a driving part 112 for moving the transport catcher part 111. The transport catcher part 111 is movable in the moving region 110a by the drive of the driving part 112, and transports the cuvette 200 among the cuvette conveying section 60, the warming section 100, and a measurement mounting part 131 of the optical information obtaining section 130. A vibrating function is provided to the transport catcher part 111, whereby the sample and the reagent in the cuvette 200 can be stirred by vibrating the cuvette 200 while gripping the cuvette 200.

As shown in FIGS. 3 to 5, the reagent dispensing arm 120 is arranged to mix the reagent to the sample in the cuvette 200 by dispensing the reagent in the reagent container 300 mounted in the reagent storing section 6 into the cuvette 200. Specifically, the reagent is aspirated through hole 22a, 22b, 22c or 22d (see FIG. 3) of the outer wall part 20 of the reagent storing section 6, and the transport catcher part 111 takes out the cuvette 200 in which warming (37° C.) is completed from the cuvette holder 101a of the warming section 100 and dispenses the aspirated regent into the cuvette 200 in a gripping state. A warming function is provided to a pipette part 121 of the reagent dispensing arm 120, and the aspirated reagent is instantaneously warmed to about 37° C. That is, the reagent stored at low temperature (about 10° C.) in the reagent storing section 6 is mixed with the sample of about 37° C., which warming is completed, while being warmed to about 37° C. by the reagent dispensing arm 120.

In the present embodiment, the reagent dispensing arm 120 is configured to move the pipette part 121 in the up and down direction through pulse control by a stepping motor (not shown) when performing the dispensing operation.

In the present embodiment, when replacement of the reagent is instructed during the operation of the reagent dispensing arm 120, the dispensing task of the reagent to be dispensed by the reagent dispensing arm 120 from the reagent table containing the specified reagent is stopped if the dispensing task of the reagent to be dispensed is carried out from the reagent table containing the specified reagent. In this case, if the reagent to be dispensed is also contained in the reagent table different from the reagent table containing the specified reagent, the reagent dispensing arm 120 stops the dispensing task of the reagent to be dispensed of the reagent table containing the specified reagent, and continues the dispensing task from the reagent to be dispensed contained in the other reagent table. If the reagent to be dispensed is arranged only in the reagent table containing the reagent instructed to be replaced, the reagent dispensing arm 120 does not to perform the dispensing operation after finishing the dispensing of the reagent to be dispensed with respect to the sample (sample waiting to be dispensed with reagent) being warmed in the warming section 100 in time of replacement instruction. Therefore, even for the sample that is being warmed in the warming section 100 in time of replacement instruction, the measurement is performed within a constant time after warming.

The optical information obtaining section 130 has a function of obtaining the optical information from the measurement sample. As shown in FIG. 5, the optical information obtaining section 130 is configured by the measurement mounting part 131 and a detecting part 132 arranged below the measurement mounting part 131.

The detecting part 132 of the optical information obtaining section 130 is configured so as to perform optical measurement (actual measurement) under a plurality of conditions on the measurement sample in the cuvette 200. The optical information obtaining section 130 is electrically connected to the control section 4a of the control device 4 and transmits the obtained data (optical information) to the control section 4a of the control device 4. In the control device 4, the data (optical information) transmitted from the optical information obtaining section 130 is analyzed, and displayed on the display 4b.

As shown in FIGS. 3 to 5, the urgent sample setting section 140 is arranged to perform sample analyzing process on the urgent sample. The urgent sample setting section 140 is configured to cut the urgent sample in when the sample analyzing process is being performed on the sample supplied from the conveyance mechanism unit 3. The urgent sample setting section 140 is slidable in the X direction and is arranged with five holders 141 for holding the container (not shown) containing diluting fluid and cleaning fluid. A barcode (not shown) is attached to the container (not shown) containing the diluting fluid and the cleaning fluid. The barcodes of the diluting fluid and the cleaning fluid are configured so as to be read by the barcode reader 351 while the urgent sample setting section 140 is being slided in the X direction. Thus, the type, arrangement, and the like of the diluting fluid and the cleaning fluid are displayed as a diluting/cleaning fluid mark 423 of the reagent managing screen 410. As shown in FIGS. 1 and 2, a lid 1c is arranged on the front surface side of the reagent replacing section 7 of the sample analyzer 1. The container (not shown) containing the diluting fluid and the cleaning fluid is replaced or added through the lid 1c.

The cuvette supply mechanism section 160 is configured to sequentially supply the plurality of cuvettes 200 randomly placed by the user to the cuvette conveying section 60. As shown in FIGS. 3 to 5, the cuvette supply mechanism section 160 includes a first hopper 161a; a second hopper 161b, smaller than the first hopper 161a, being supplied with the cuvette 200 from the first hopper 161a; two induction plates 162 supplied with the cuvette 200 from the second hopper 161b; a supporting table 163 arranged on the lower end of the two induction plates 162; and a supply catcher part 164 arranged at a predetermined distance from the supporting table 163. The cuvette 200 supplied to the first hopper 161a is slidably moved towards the supporting table 163 on the induction plates 162 by way of the second hopper 161b smaller than the first hopper 161a. The supporting table 163 has a function of rotatably transporting the cuvette 200 slidably moved on the induction plates 162 to a position allowing the supply catcher part 164 to grip the cuvette 200. The supply catcher part 164 is arranged to supply the cuvette 200 rotatably transported by the supporting table 163 to the cuvette conveying section 60.

Furthermore, as shown in FIGS. 3 to 5, the measurement mechanism unit 2 includes a discarding hole 171 (see FIGS. 3 and 5) for discarding the cuvette 200 and a discarding box 172 arranged below the discarding hole 171 are arranged at a predetermined spacing from the supply catcher part 164 described above. The supply catcher part 164 can discard the cuvette 200 on a cuvette conveying table 61 of the cuvette conveying section 60 to the discarding box 172 through the discarding hole 171 (see FIGS. 3 and 5). That is, the supply catcher part 164 can both supply and discard the cuvette 200.

Figure 16:
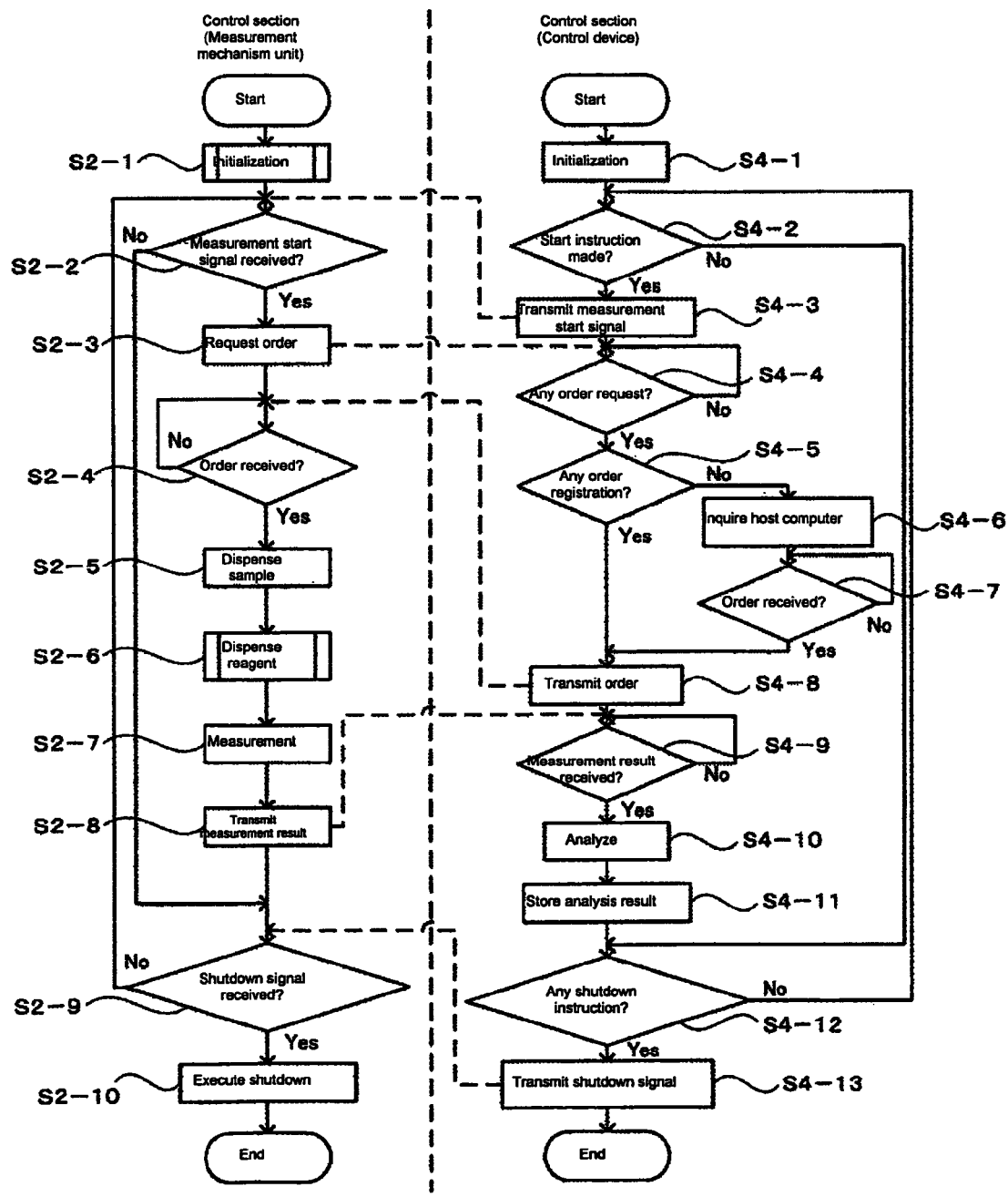
FIG. 16 is a flowchart showing a measurement process flow of the control section 4a of the control device 4 and the control section 501 of the measurement mechanism unit 2 of the sample analyzer according to one embodiment of the present invention.

FIG. 16 is a flowchart describing the measurement process flow of the control section 4a of the control device 4 and the control section 501 of the measurement mechanism unit 2 of the sample analyzer 1 according to the present embodiment. The measurement process flow of the control section 4a and the control section 501 of the sample analyzer 1 according to the present embodiment will be described below with reference to FIG. 16.

First, when the power (not shown) of the measurement mechanism unit 2 is turned ON by the operation of the user, the control section 501 executes initialization of the measurement mechanism unit 2 (step S2-1). The initialization process of the control section 501 of step S201 will be hereinafter described. When the power (not shown) of the control device 4 is turned ON by the operation of the user, the control section 4a of the control device 4 executes initialization of the program stored in the control section 4a (step S4-1).

Figure 17:
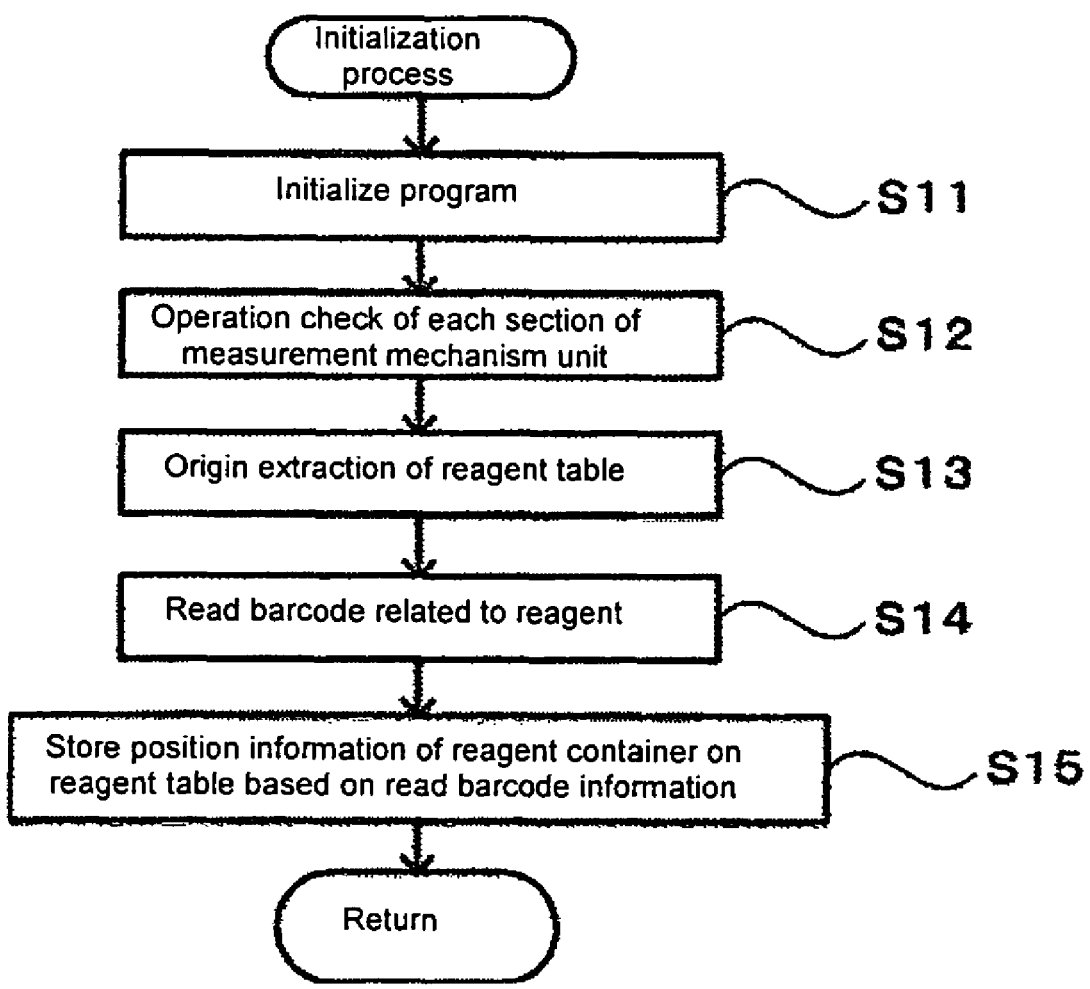
FIG. 17 is a flowchart showing an initialization process by the control section 501 of the measurement mechanism unit 2 according to one embodiment of the present invention.

The initialization process by the control section 501 of the measurement mechanism unit 2 will now be described with reference to FIG. 17.

First, the control section 501 executes initialization of the program stored in the control section 501 (step S11). The control section 501 then executes an operation check of each section of the measurement mechanism unit 2 (step S12). The operation for returning the mechanism for moving the cuvette 200 and each dispensing arm (sample dispensing arm 70 and regent dispensing arm 120) to the initial position is thereby performed. The control section 501 then executes origin extraction of the first reagent table 11 and the second reagent table 12 (step S13). The first reagent table 11 and the second reagent table 12 thereby rotate up to the origin position and then stop. Subsequently, the control section 501 requests for an initialization completed signal indicating the completion of initialization of the control section 4a, and when receiving such initialization completed signal, controls the reagent barcode reader 350 to read the barcodes of all the reagents set in the reagent storing section 6, the barcode of the reagent container rack, and the barcode of the holder of the reagent container rack (step S14). The control section 501 determines the position information of each reagent container on the first reagent table 11 and the second reagent table 12 based on the read barcode information, and stores the determined position information and barcode information in the RAM 501c (step S15). The read barcode information and position information are transmitted from the control section 501 to the control section 4a, and stored in the hard disc 401d of the control section 4a.

A method of determining the position information of each reagent container on the reagent table (first reagent table 11 and second reagent table 12) in step S15 will be described. In the present embodiment, a reference position is arranged at a predetermined position of every arrangement region (five for each of the first reagent table 11 and the second reagent table 12) of each reagent container rack in the reagent table. The shifted amount between each holder of the arranged reagent container rack and the reference position is defined in advance as a design value for each type of reagent container rack. The shifted amount from the origin position of the reagent table to each reference position is also defined in advance as a design value. Thus, the shifted amount from the origin position of the reagent table to each reagent container of the reagent table can be calculated from the shifted amount from the origin position of the reagent table to each reference position and the shifted amount of each holder of the arranged reagent container rack and the reference position. The position information of each reagent container of the reagent table is thereby determined. Such shifted amounts are expressed with a value of a rotation angle of the reagent table.

The control section 4a of the control device 4 then determines whether or not a start button displayed on a menu screen (not shown) displayed on the display 4b has been pushed by the user (step S4-2), and transmits a measurement start signal to the control section 501 if the start button has been pressed (step S4-3). The process proceeds to step S4-12 if the start button has not been pressed in step S4-2.

The control section 501 of the measurement mechanism unit 2 then determines whether or not the measurement start signal has been received (step S2-2). The control section 501 proceeds to step S2-9 if the measurement start signal has not been received.

If the measurement start signal has been received, the control section 501 controls the conveyance mechanism unit 3 so that the rack 251 mounted with the test tube 250 containing the sample is moved up to the position corresponding to the aspirating position 2a of the measurement mechanism unit 2. The control section 501 then controls the sample barcode reader 3c so that the barcode of the test tube 250 mounted on the rack 251 is read. The control section 501 makes a request for order information to the control section 4a of the control device 4 based on the read barcode information (step S2-3). The order information is information including analysis items corresponded to the information specifying the sample. The order information may be registered in a host computer (not shown) connected to the control device 4, or may be stored by being manually input by the user to the control device 4.

The control section 4a of the control device 4 determines whether or not the order request has been made (step S4-4), and determines whether or not the order information is registered in the hard disc 401d of the control section 4a if the order request has been made (step S4-5). When the order information is registered in the hard disc 401d, the control section 4a transmits the registered order information to the control section 501 of the measurement mechanism unit 2 (step S4-6). If the order information has not been registered in the hard disc 401d, the control section 4a makes an inquiry on order registration to the host computer based on the barcode information of the sample read by the sample barcode reader 3c (step S4-7). When receiving the order information from the host computer (step S4-8), the control section 4a transmits the received order information to the control section 501 of the measurement mechanism unit 2 (step S4-6).

When receiving the order information from the control section 4a (step S2-4), the control section 501 of the measurement mechanism unit 2 causes the sample dispensing arm 70 to dispense the sample (step S2-5). Specifically, the control section 501 causes the sample dispensing arm 70 to aspirate the sample of a predetermined amount from the test tube 250. The sample dispensing arm 70 is then moved to the upper side of the cuvette 200 held by the cuvette conveying table 61 of the cuvette conveying section 60. Thereafter, the sample in the cuvette 200 is discharged from the sample dispensing arm 70. The control section 501 then drives the reagent dispensing arm 130 according to the order information, and adds the reagent in the reagent container 300 mounted on the reagent table (first reagent table 11 or second reagent table 12) to the sample in the cuvette 200 (step S2-6). The measurement sample is thereby prepared. The reagent dispensing process in step S2-6 will be hereinafter described. The control section 501 controls the cuvette transporting section 120 so as to move the cuvette 200 containing the measurement sample to the cuvette mounting part 141 of the optical information obtaining section 140. The detecting part 142 of the optical information obtaining section 140 is controlled so as to carry out optical measurement under a plurality of conditions with respect to the measurement sample in the cuvette 200, whereby optical information is obtained from the measurement sample (step S2-7). The control section 501 sequentially transmits the obtained optical information to the control section 4a of the control device 4 (step S2-9). The steps S2-5, S2-6, and S2-7 in the control section 501 are parallel processed.

When receiving the measurement result from the control section 501 (step S4-9), the control section 4a of the control device 4 analyzes the received measurement result (step S4-10), and stores the obtained analysis result in the hard disc 401d of the control section 4a (step S4-11).

The control section 4a determines whether or not instruction of shutdown has been made (whether or not the user has pushed the shutdown button (not shown) from the menu screen) (step S4-12), where a shutdown signal is transmitted from the control section 4a to the control section 501 if the instruction of shutdown has been made (step S4-13), and the shutdown of the control device 4 is performed. The process returns to step S4-2 if instruction of shutdown has not been made.

The control section 501 of the measurement mechanism unit 2 then determines whether or not the shutdown signal has been received (step S2-9), and executes the shutdown of the measurement mechanism unit 2 if the shutdown signal has been received (step S2-10). The process returns to step S2-2 if the shutdown signal has not been received.

Figure 18:
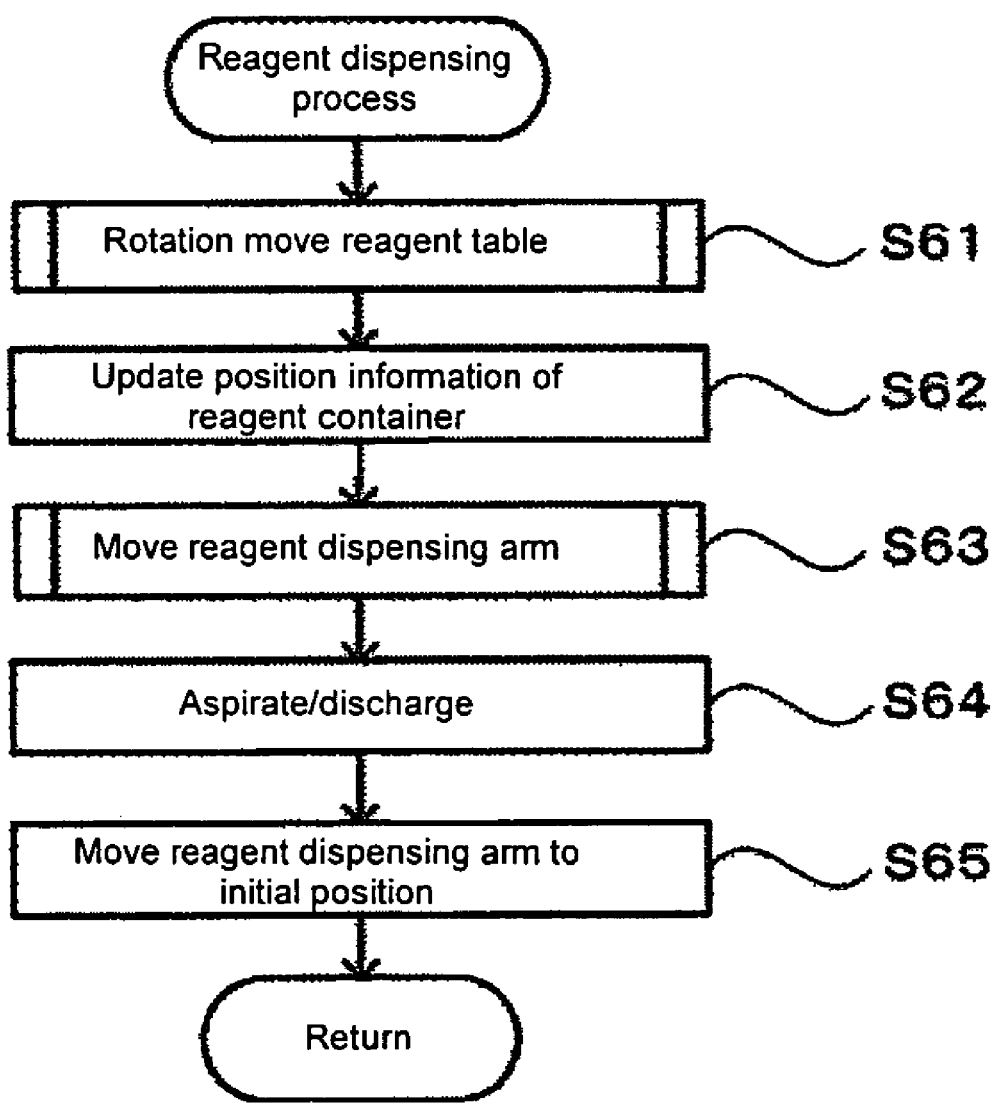
FIG. 18 is a flowchart showing a reagent dispensing process by the control section 501 of the measurement mechanism unit 2 according to one embodiment of the present invention.

The reagent dispensing process in step S2-6 will now be described with reference to FIG. 18.

In the present embodiment, the reagent table is configured to be rotation movable in the horizontal direction, and the reagent dispensing arm 120 is also configured to be rotation movable in the horizontal direction. Thus, the reagent dispensing arm 120 can aspirate the reagent at the reagent aspirating position defined by an intersecting position of a trajectory of rotation movement of the center point of the reagent container arranged on the reagent table and the trajectory of rotation movement of the reagent dispensing arm 120.

Two types of reagent containers racks (second reagent container rack 320 and third reagent container rack 330) of different rack types can be arranged on the second reagent table 12. As shown in FIGS. 12 and 13, the shapes of the outer shape of the second reagent container rack 320 of rack type 1 and the third reagent container rack 330 of rack type 2 are the same, but the number of holders (holders) in the second reagent container rack 320 of rack type 1 and the number of holders (holders) in the third reagent container rack 330 of rack type 2 differ. Since the number of holders in the reagent container rack of both types differs, the position of the holder in the second reagent container rack 320 of rack type 1 and the position of the holder in the third reagent container rack 330 of rack type 2 differ.

The holder is concentrically arranged in the reagent container rack of both types, but the trajectory on which the center point of each holder of the back column (inner peripheral side) of the second reagent container rack 320 of rack type 1 rotation moves and the trajectory on which the center point of each holder of the back column of the third reagent container rack 330 of rack type 2 rotation moves differ. The trajectory on which the center point of each holder of the front column (outer peripheral side) of the second reagent container rack 320 of rack type 1 rotation moves and the trajectory on which the center point of each holder of the front column of the third reagent container rack 330 of rack type 2 rotation moves are the same. The reagent aspirating position for aspirating the reagent from the reagent container held in each holder of the front column (outer peripheral side) of the reagent container racks of rack type 1 and rack type 2, that is, the intersecting position of the trajectory of rotation movement of the center point of each holder of the front column and the trajectory of rotation movement of the reagent dispensing arm 120 is referred to as "reagent aspirating position A". The reagent aspirating position for aspirating the reagent from the reagent container held in each holder of the back column (inner peripheral side) of the second reagent container rack 320 of rack type 1, that is, the intersecting position of the trajectory of rotation movement of the center point of each holder of the back column of the second reagent container rack 320 and the trajectory of rotation movement of the first reagent dispensing arm 120 is referred to as "reagent aspirating position B". Similarly, the reagent aspirating position for aspirating the reagent from the reagent container held in each holder of the back column (inner peripheral side) of the third reagent container rack 330 of rack type 2, that is, the intersecting position of the trajectory of rotation movement of the center point of each holder of the back column of the third reagent container rack 330 and the trajectory of rotation movement of the reagent dispensing arm 120 is referred to as "reagent aspirating position C". In the present embodiment, only the first reagent container rack 310 shown in FIG. 8 is arranged in the first reagent table 11, and thus the reagent aspirating position for aspirating the reagent from the reagent container held in the holder of the first reagent container rack 310 arranged in the first reagent table 11, that is, the intersecting position of the trajectory of rotation movement of the center point of each holder of the first reagent container rack 310 and the trajectory of rotation movement of the reagent dispensing arm 120 is referred to as "reagent aspirating position D".

In the reagent dispensing process in step S2-6, the control section 501 firstly rotation moves the reagent table (first reagent table 11 or second reagent table 12) so that the reagent container (hereinafter referred to as "reagent container R") containing the reagent to be dispensed corresponding to the analysis items of the sample moves to the reagent aspirating position by the reagent dispensing arm 120 according to the order information (step S61).

Figure 19:
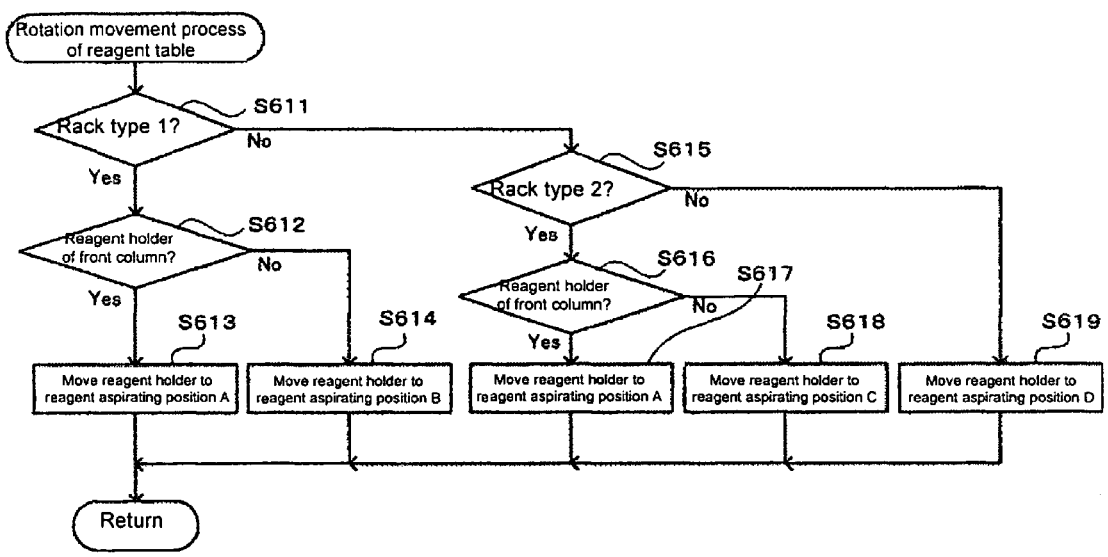
FIG. 19 is a flowchart showing a rotation movement process of the reagent table by the control section 501 of the measurement mechanism unit 2 according to one embodiment of the present invention.

The rotation movement process in step S61 will be described below using FIG. 19. The control section 501 firstly determines whether or not the reagent container rack holding the reagent container R is the reagent container rack of rack type 1 based on the barcode information and the position information stored in the RAM 501 C (step S611). If the reagent container rack holding the reagent container R is the reagent container rack of rack type 1, the control section 501 then determines whether or not the holder holding the reagent container R is the holder on the front column (outer peripheral side) in the reagent container rack (step S612). If the holder holding the reagent container R is the holder of the front column in the reagent container rack, the control section 501 provides the driving pulse signal of a number of pulse N1 to the second driving section 503 and rotates the second reagent table 12 so that the holder holding reagent container R moves to the reagent aspirating position A (step S613).

The number of pulse N of the driving pulse signal provided from the control section 501 to the driving section (first driving section 502 or second driving section 503) is obtained by the following equation (1).

$$N = (L - M)/S \qquad (1)$$

"L" represents position information of the reagent container R on the reagent table (first reagent table 11 and second reagent table 12), that is, shifted amount from the origin position of the reagent table to the reagent container R as a value of the rotation angle of the reagent table. The value of "L" is also changed according to the rotation of the reagent table to change the position information of the reagent container R according to the rotation of the reagent table. "M" represents the shifted amount from the origin position of the reagent table to the reagent aspirating position by the reagent dispensing arm 120 as a value of the rotation angle of the reagent table. Thus, "L−M" represents the shifted mount from the reagent container R to the reagent aspirating position by the reagent dispensing arm 120 as a value of the rotation angle of the reagent table. "S" represents the step angle (rotation angle per one pulse) of the first stepping motor of the first driving section 502 and the second stepping motor of the second driving section 503. In equation (1), the rotation angle in the clockwise direction takes a positive value.

In the present embodiment, whether or not the value of "L−M" used in equation (1) is lower than or equal to 180, that is, $$L - M \leq 180 \qquad (2)$$

is determined by the control section 501. If determined that equation (2) is met, the reagent table is rotated by the number of pulse N in the counterclockwise direction. If determined that equation (2) is not met, the reagent table is rotated by the number of pulse in the clockwise direction by $$(360/S) - N \qquad (3)$$

The number of pulse N1 of the driving pulse signal provided from the control section 501 to the second driving section 503, and the rotating direction of the second reagent table 12 are determined in step S613 using equations (1), (2), and (3).

If determined that the reagent holder holding the reagent container R is not the reagent holder of the front column in the reagent container rack in step S612, the control section 501 provides a driving pulse signal of a number of pulse N2 to the second driving section 503 and rotates the second reagent table 12 (step S614) so that the reagent holder holding the reagent container R moves to the reagent aspirating position B, and returns the process. The number of pulse N2 and the rotating direction of the second reagent table 12 are determined by the above equations (1) to (3).

If determined that the reagent container rack holding the reagent container R is not the reagent container rack of rack type 1 in step S611, determination is made on whether or not the reagent container rack holding the reagent container R is the reagent container rack of rack type 2 (step S615). If the reagent container rack holding the reagent container R is the reagent container rack of rack type 2, determination is then made on whether or not the holder holding the reagent container R is the holder of the front column in the reagent container rack (step S616). If the holder holding the reagent container R is the holder of the front column in the reagent container rack, the control section 501 provides a driving pulse signal of a number of pulse N3 to the second driving section 503 and rotates the second reagent table 12 so that the reagent container R moves to the reagent aspirating position A (step S617). The number of pulse N3 and the rotating direction of the second reagent table 12 are determined by the above equations (1) to (3). If determined that the holder holding the reagent container R is not the holder of the front column in the reagent container rack in step S616, the control section 501 provides a driving pulse signal of a number of pulse N4 to the second driving section 503 and rotates the second reagent table 12 (step S618) so that the reagent container R moves to the reagent aspirating position C, and returns the process. The number of pulse N4 and the rotating direction of the second reagent table 12 are also determined by the above equations (1) to (3).

If determined that the reagent container rack holding the reagent container R is not the reagent container rack of rack type 2 in step S615, the control section 501 provides a driving pulse of a pulse number N5 to the first driving section 502 and rotates the first reagent table 11 (step S619) so that the reagent container R moves to the reagent aspirating position D, and returns the process. The number of pulse N5 and the rotating direction of the first reagent table 11 are also determined by the above equations (1) to (3).

After the rotation movement process of the reagent table in step S61, the control section 501 updates the position information of each reagent container on the reagent table to the position information after the rotation movement process of the reagent table (step S62). The updating of the position information of each reagent container is performed based on the rotation angle of the reagent container R and the position information of each reagent container before the rotation movement process of the reagent table.

Figure 20:
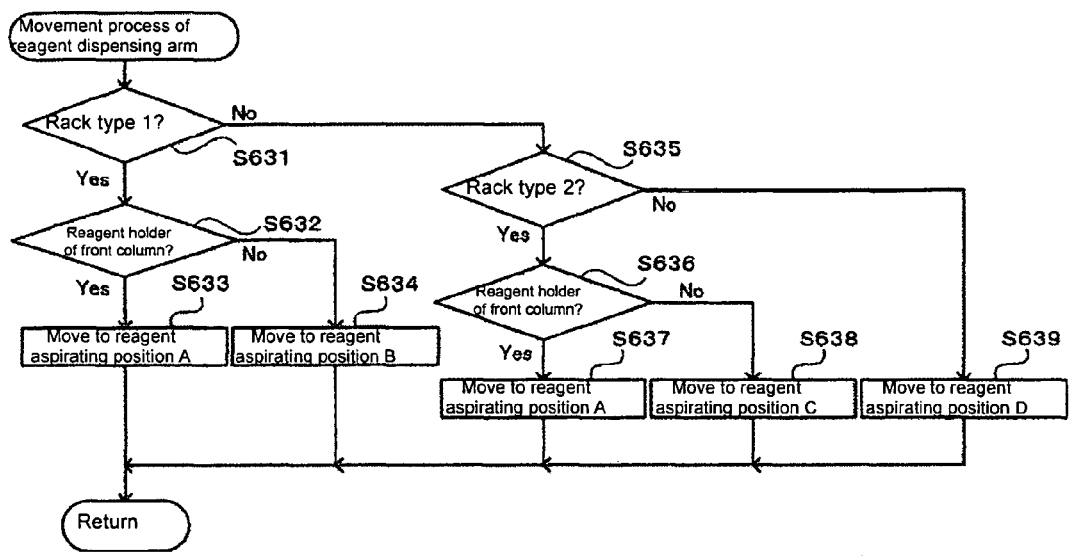
FIG. 20 is a flowchart showing a movement process of the reagent dispensing arm by the control section 501 of the measurement mechanism unit 2 according to one embodiment of the present invention.

The control section 501 then drives the reagent dispensing driving section 120a so that the reagent dispensing arm 120 moves to the reagent aspirating position (step S63). The movement process of the reagent dispensing arm 120 will now be described with reference to FIG. 20.

The control section 501 first determines whether or not the reagent container rack holding the reagent container (reagent container R) containing the reagent to be dispensed corresponding to the analysis items of the sample is the reagent container rack of rack type 1 based on the barcode information stored in the control section 4a of the control device 4 (step S631). If the reagent container rack holding the reagent container R is the reagent container rack of rack type 1, determination is then made on whether or not the holder holding the reagent container R is the holder of the front column in the reagent container rack (step S632). If the holder holding the reagent container R is the holder of the front column in the reagent container rack, the reagent dispensing driving section 120a is driven so that the reagent dispensing arm 120 moves to the reagent aspirating position A (step S633).

If the holder holding the reagent container R is not the holder of the front column in the reagent container rack in step S632, the control section 501 drives the reagent dispensing driving section 120a (step S614) so that the reagent dispensing arm 120 moves to the reagent aspirating position B, and returns the process.

If the reagent container rack holding the reagent container R is not the reagent container rack of rack type 1 in step S631, determination is then made on whether or not the reagent container rack holding the reagent container R is the reagent container rack of rack type 2 (step S635). If the reagent container rack holding the reagent container R is the reagent container rack of rack type 2, determination is then made on whether or not the holder holding the reagent container R is the holder of the front column in the reagent container rack (step S636). If the holder holding the reagent container R is the holder of the front column in the reagent container rack, the control section 501 drives the reagent dispensing driving section 120a (step S637) so that the reagent dispensing arm 120 moves to the reagent aspirating position A. If determined that the holder holding the reagent container R is not the holder of the front column in the reagent container rack in step S636, the control section 501 drives the reagent dispensing driving section 120a (step S638) so that the reagent dispensing arm 120 moves to the reagent aspirating position C, and returns the process.

If determined that the reagent container rack holding the reagent container R is not the reagent container rack of type 2 in step S635, the control section 501 drives the reagent dispensing driving section 120a (step S639) so that the reagent dispensing arm 120 moves to the reagent aspirating position D, and returns the process.

The control section 501 then drives the reagent dispensing driving section 120a (step S64) so that the reagent dispensing arm 120 that has moved to the reagent aspirating position aspirates the reagent from the reagent container R and thereafter discharges the aspirated reagent to the cuvette 200 at the predetermined position. The control section 501 then drives the reagent dispensing driving section 120a (step S65) so that the reagent dispensing arm 120 moves to the initial position. Thereafter, the control section 501 returns the process.

As described, in the present embodiment, the driving section of the reagent table and the reagent dispensing driving section 120a are controlled by the control section 501 so that the reagent container containing the reagent to be dispensed and the reagent dispensing arm 120 move to the reagent aspirating position corresponding to the type of reagent container rack. Therefore, even if a plurality of reagent container racks having different number of holders for holding the reagent container and a plurality of reagent container rack having different positions of the holder are arranged on the reagent table, the reagent can be easily aspirated from the reagent container held in the reagent container rack. This contributes to increasing the number of measurement items and enhancing the processing speed.

In the present embodiment, the size of the reagent container held in the reagent container rack can be changed depending on the type of reagent container rack. Thus, reagent containers of various sizes can be used depending on the usage state of the reagent.

In the present embodiment, the reagent aspirating position where the reagent is aspirated from the reagent container held in the reagent container rack is determined based on the identification information specifying the reagent container rack. Thus, information related to the reagent aspirating position does not need to be recorded in advance in the barcode of each reagent container and the barcode of each reagent container rack, and analysis of multiple items can be immediately responded.

In the present embodiment, a greater number of reagent containers can be arranged on the reagent table since the first reagent table 11 and the second reagent table 12 which are rotation movable and which can arrange the reagent container rack are concentrically arranged.

Furthermore, in the present embodiment, the outer shape of the second reagent container rack 320 and the outer shape of the third reagent container rack 330 capable of being arranged on the second reagent table 12 are formed so as to be the same. Thus, the reagent container rack to be arranged at a predetermined arrangement region of the second reagent table 12 can be freely selected from the second reagent container rack 320 and the third reagent container rack 330.

In the present embodiment, the second reagent container rack 320 and the third reagent container rack 330 are configured to be able to hold the reagent containers 300 in a zig-zag manner. Accordingly, a greater amount of reagent containers 300 can be held at the second reagent container rack 320 and the third reagent container rack 330, and reading of the barcode 300a of the reagent container 300 can be satisfactorily carried out by the reagent barcode reader 350.

In the present embodiment, the reagent container 300 is concentrically arranged in the second reagent container rack 320 and the third reagent container rack 330. Thus, each holder of the front column (outer peripheral side) of the second reagent container rack 320 rotation moves on the same trajectory and each holder of the back column (inner peripheral side) rotation moves on the same trajectory by the rotation movement of the second reagent table 12. Furthermore, each holder of the front column (outer peripheral side) of the third reagent container rack 330 rotation moves on the same trajectory and each holder of the back column (inner peripheral side) rotation moves on the same trajectory by the rotation movement of the second reagent table 12. Thus, control of the reagent dispensing process is facilitated.

In the present embodiment, the reagent dispensing arm 120 is configured to the rotation movable in the horizontal direction and the reagent aspirating position by the reagent dispensing arm 120 is at the intersecting position of the trajectory of the rotation movement of the reagent dispensing arm 120 and the trajectory of the rotation movement of the reagent table. Thus, the drive control of the reagent dispensing arm 120 is facilitated.

The embodiments disclosed herein are illustrative and should not be construed as being restrictive in all aspects. The scope of the invention is defined by the appended Claims rather than by the description of the embodiments, and all changes that fall within meets and bounds of the claims, or equivalence of such meets and bounds are therefore intended to be embraced by the claims.

For instance, the reagent container rack 310 of the same type is arranged in the first reagent table 11 in the above embodiment, but the reagent container rack of another type having different number of holders for holding the reagent container may be arranged. The reagent container rack of another type having different positions of the holder may be arranged in the first reagent table 11.

Figure 21:
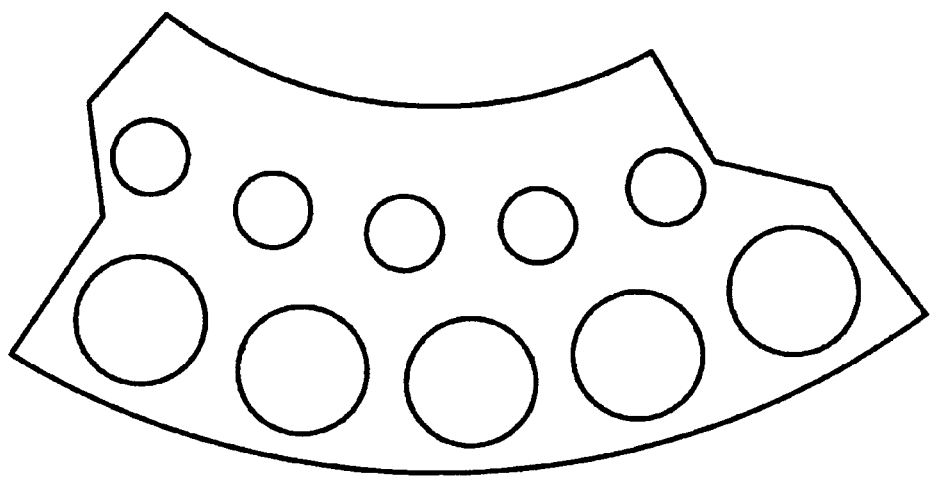
FIG. 21 is a schematic view showing a reagent container rack of rack type 3.

In the above embodiment, the second reagent container rack 320 of rack type 1 and the third reagent container rack 330 of rack type 2 are arranged in the second reagent table 12, but the reagent container rack of rack type 3 having different number and position of the holder from the rack type 1 and the rack type 2 may be arranged in place of the reagent container rack of rack type 1, as shown in FIG. 21, or the reagent container rack of rack type 3 may be arranged in place of the reagent container rack of rack type 2. Moreover, the reagent container rack of rack type 3 may be arranged in addition to the reagent container rack of rack type 1 and rack type 2. The reagent container rack of another type having different number and position of the holder from rack types 1 to 3 may be arranged.

In the above embodiment, each of the first reagent table 11 and the second reagent table 12 is configured so that five reagent container racks can be arranged, but the first reagent table 11 and the second reagent table 12 may be configured so that five or more reagent container racks can be arranged.

In the above embodiment, the holders (holders) are concentrically arranged in the second reagent container rack 320 and the third reagent container rack 330, but the holders are not necessarily concentrically arranged.

In the above embodiment, the reagent dispensing arm 120 is rotation movable in the horizontal direction, but the reagent dispensing arm 120 may be configured to be movable in the XY direction.

In the embodiment, the first reagent table 11 and the second reagent table 12 are configured to a ring shape, but are not necessarily formed to a ring shape, and may be formed to a square.

In the above embodiment, the first reagent table 11 and the second reagent table 12 are rotated, but are not necessarily rotated.

In the embodiment, the reagent container rack including a plurality of holders is arranged in the first reagent table 11 and the second reagent table 12, but the reagent container rack including only one holder at a predetermined position may be arranged in the first reagent table 11 and the second regent table 12. In this case, the position of the reagent container on the reagent table can be specified without reading the barcode of the holder, and thus the control of the reagent dispensing process can be more easily performed.

In the above embodiment, the barcode of each holder of the reagent container rack arranged in the first reagent table 11 and the second reagent table 12 is read, but the barcode of each holder of the reagent container rack does not need to be read if the type of reagent held in each holder of the reagent container rack is determined in advance. In this case as well, the position of the reagent container containing the reagent to be aspirated can be specified.

What is claimed is:

1. A sample analyzer for analyzing a sample using a reagent corresponding to a predetermined analysis item, comprising:
    a table configured to hold a first rack and a second rack, each of the first and second racks comprising a rack identifier and a plurality of reagent container holders, wherein a number of the reagent container holders of the first rack is different from a number of the reagent container holders of the second rack;
    a table rotating part configured to move the table;
    an aspirator which comprises an aspirating pipette in which a reagent from a reagent container held by a reagent container holder is aspirated and a driver configured to move the aspirating pipette;
    an identification information obtainer configured to obtain identification information of a rack holding a target reagent container which contains a target reagent used for analysis, from a rack identifier of the rack;
    a controller configured to determine a type of the rack holding the target reagent container based on the identification information obtained by the identification information obtainer, to control the driver so as to move the aspirating pipette to a predetermined reagent aspirating position according to the determined type of the rack holding the target reagent container and to control the table rotating part so as to move the target reagent container to the reagent aspirating position; and
    an analyzing section configured to analyze a sample using the target reagent aspirated by the aspirating pipette at the reagent aspirating position.

2. The sample analyzer of claim 1, wherein
    the identification information, obtained from the rack identifier by the identification information obtainer, includes information specifying a type of the rack.

3. The sample analyzer of claim 1, wherein,
    the table rotating part is configured to rotate the table.

4. The sample analyzer of claim 1, wherein
the controller;
controls the driver so as to move the aspirating pipette to a first reagent aspirating position and controls the table rotating part so as to move the target reagent container to the first reagent aspirating position, when the rack holding the target reagent container is the first rack; and
controls the driver so as to move the aspirating pipette to a second reagent aspirating position different from the first reagent aspirating position and controls the table rotating part so as to move the target reagent container to the second reagent aspirating position, when the rack holding the target reagent container is the second rack.

5. The sample analyzer of claim 1, wherein
each of the reagent container holders of the first rack is configured to hold a reagent container which comprises a reagent identifier;
each of the reagent container holders of the second rack is configured to hold a reagent container which comprises a reagent identifier;
the identification information obtainer obtains an identification information which specifies a reagent contained in a reagent container on the table from a reagent identifier of the reagent container on the table; and
the controller obtains a position information of the target reagent container on the table based on the identification information obtained by the identification information obtainer and
controls the table rotating part so as to move the target reagent container to the predetermined reagent aspirating position based on the position information of the target reagent container on the table.

6. The sample analyzer of claim 1, wherein
the number of the reagent container holders of the first rack is greater than the number of the reagent container holders of the second rack, and a size of each reagent container holder of the first rack is smaller than a size of each reagent container holder of the second rack.

7. The sample analyzer of claim 1, wherein
the first rack has the same outer shape as that of the second reagent container rack.

8. The sample analyzer of claim 1, wherein
the first and second racks respectively arranges the reagent container holders concentrically.

9. The sample analyzer of claim 8, wherein
each of the reagent container holders of the first rack is moved to the first reagent aspirating positions, and each of the reagent container holders of the second rack is moved to the second reagent aspirating position; and
the first rack comprises a plurality of second reagent container holders arranged on a circular arc of a concentric circle with the table, each of the second reagent container holders being moved to a third reagent aspirating position different from the first and second reagent aspirating positions.

10. The sample analyzer of claim 9, wherein
the reagent container holders and the second reagent container holders of the first rack are arranged in zig-zag manner.

11. The sample analyzer of claim 5, wherein
the controller obtains a value indicating a rotation angle of the table from an origin position of the table to the target reagent container on the table as the position information of the target reagent container.

12. The sample analyzer of claim 1, wherein
each of the reagent container holders of the first and second racks comprises a holder identifier; and
the identification information obtainer obtains identification information specifying each of the reagent container holders from the holder identifiers of the reagent container holders of the first and second racks.

13. The sample analyzer of claim 1, wherein
the aspirating pipette is capable of rotating in a horizontal plane; and
the first reagent aspirating position is an intersecting position of a trajectory of a rotation movement of the aspirating pipette and a trajectory of a rotation movement of the reagent container holders of the first rack by a rotation movement of the table, and
the second reagent aspirating position is an intersecting position of a trajectory of the rotation movement of the aspirating pipette and a trajectory of a rotation movement of the reagent container holders of the second rack by the rotation movement of the table.

14. The sample analyzer of claim 1, further comprising
a memory that stores a position information of each reagent container holder of the first and second racks.

15. The sample analyzer of claim 4, wherein
the table is formed as a circular rotating table, and
the sample analyzer further comprising
a second table being arranged inside the table concentrically, being rotatable independent from the table and being capable of holding a third rack,
wherein
the third rack comprises a rack identifier and a reagent container holder configured to hold a reagent container, the reagent container holder being moved to a third reagent aspirating position different from the first and second reagent aspirating positions and having a holder identifier.

16. The sample analyzer of claim 5, wherein
the rack identifiers of the first and second racks, and the reagent identifiers of the reagent containers held in the first and second racks are barcodes.

17. The sample analyzer of claim 1, wherein
the controller obtains an order information including analysis items of the sample,
the analyzing section is configured to analyze the sample according to the order information obtained by the controller.

18. The sample analyzer of claim 17, wherein
the sample is a blood sample; and
the analyzing section performs analysis related to coagulation function of the blood sample.

* * * * *